US010722250B2

(12) United States Patent
Tasci et al.

(10) Patent No.: US 10,722,250 B2
(45) Date of Patent: Jul. 28, 2020

(54) MAGNETIC-FIELD DRIVEN COLLOIDAL MICROBOTS, METHODS FOR FORMING AND USING THE SAME

(71) Applicant: Colorado School of Mines, Golden, CO (US)

(72) Inventors: Tonguc Onur Tasci, Golden, CO (US); Keith B. Neeves, Denver, CO (US); David W. M. Marr, Golden, CO (US)

(73) Assignee: Colorado School of Mines, Golden, CO (US)

( * ) Notice: Subject to any disclaimer, the term of this patent is extended or adjusted under 35 U.S.C. 154(b) by 380 days.

(21) Appl. No.: 15/069,681

(22) Filed: Mar. 14, 2016

(65) Prior Publication Data

US 2016/0263391 A1    Sep. 15, 2016

Related U.S. Application Data

(60) Provisional application No. 62/132,682, filed on Mar. 13, 2015.

(51) Int. Cl.
*A61B 17/22* (2006.01)
*A61B 34/00* (2016.01)
(Continued)

(52) U.S. Cl.
CPC .......... *A61B 17/22* (2013.01); *A61B 17/3207* (2013.01); *A61B 34/72* (2016.02);
(Continued)

(58) Field of Classification Search
CPC .. A61N 2/12; A61B 2017/00345; A61B 34/73
See application file for complete search history.

(56) References Cited

U.S. PATENT DOCUMENTS

| 2,880,326 A | 3/1959 | Musicant |
| 4,190,535 A | 2/1980 | Luderer |

(Continued)

FOREIGN PATENT DOCUMENTS

| DE | 19712309 | 5/1998 |
| EP | 1221342 | 7/2002 |

(Continued)

OTHER PUBLICATIONS

"Fiber Coupled LED Source and Accessories" http://www.wttechnology.com/LED.htm, printed May 16, 2011, 1 page.
(Continued)

*Primary Examiner* — Christine H Matthews
(74) *Attorney, Agent, or Firm* — Sheridan Ross, P.C.

(57) ABSTRACT

The invention relates to a magnetic-field driven colloidal microbot that employs wall-based propulsion, method of forming the microbot and a method of using the microbot. The microbot can be formed in situ with the use of magnetic fields, and the magnetic fields can be used to translate the microbot to a specified location in a patient. The microbot does not depend on "swimming" or flow currents within a patient to move, but instead can propel itself along a surface using a magnetic field. Once the magnetic field is removed, the microbot disassembles into colloidal particles.

21 Claims, 19 Drawing Sheets
(5 of 19 Drawing Sheet(s) Filed in Color)

(51) Int. Cl.
 *A61B 17/3207* (2006.01)
 *A61M 37/00* (2006.01)
 *A61B 17/00* (2006.01)
 *A61B 34/30* (2016.01)

(52) U.S. Cl.
 CPC .... *A61B 34/73* (2016.02); *A61B 2017/00345* (2013.01); *A61B 2017/22082* (2013.01); *A61B 2034/303* (2016.02); *A61M 37/00* (2013.01)

(56) References Cited

U.S. PATENT DOCUMENTS

| | | |
|---|---|---|
| 5,002,647 A | 3/1991 | Tanabe et al. |
| 5,021,224 A | 6/1991 | Nakajima |
| 5,098,850 A | 3/1992 | Nishida et al. |
| 5,148,511 A | 9/1992 | Savu et al. |
| 5,176,786 A | 1/1993 | Debe |
| 5,187,089 A | 2/1993 | Scott et al. |
| 5,304,487 A | 4/1994 | Wilding et al. |
| 5,427,663 A | 6/1995 | Austin |
| 5,512,745 A | 4/1996 | Finer et al. |
| 5,541,072 A | 7/1996 | Wang et al. |
| 5,622,831 A | 4/1997 | Liberti et al. |
| 5,639,669 A | 6/1997 | Ledley |
| 5,707,799 A | 1/1998 | Hansmann et al. |
| 5,715,946 A | 2/1998 | Reichenbach |
| 5,750,339 A | 5/1998 | Smith |
| 5,753,038 A | 5/1998 | Vichr et al. |
| 5,770,029 A | 6/1998 | Nelson et al. |
| 5,837,115 A | 11/1998 | Austin |
| 5,855,753 A | 1/1999 | Trau et al. |
| 5,858,188 A | 1/1999 | Soane et al. |
| 5,866,345 A | 2/1999 | Wilding et al. |
| 5,928,880 A | 7/1999 | Wilding et al. |
| 5,952,173 A | 9/1999 | Hansmann et al. |
| 6,007,690 A | 12/1999 | Nelson |
| 6,017,390 A | 1/2000 | Charych et al. |
| 6,054,034 A | 4/2000 | Soane et al. |
| 6,055,106 A | 4/2000 | Grier et al. |
| 6,067,859 A | 5/2000 | Kas et al. |
| 6,074,827 A | 6/2000 | Nelson |
| 6,128,006 A | 10/2000 | Rosenberg et al. |
| 6,156,270 A | 12/2000 | Buechler |
| 6,187,089 B1 | 2/2001 | Phillips et al. |
| 6,197,523 B1 | 3/2001 | Rimm et al. |
| 6,221,671 B1 | 4/2001 | Groner et al. |
| 6,241,894 B1 | 6/2001 | Briggs et al. |
| 6,251,691 B1 | 6/2001 | Seul |
| 6,256,093 B1 | 7/2001 | Ravid et al. |
| 6,256,096 B1 | 7/2001 | Johnson |
| 6,265,229 B1 | 7/2001 | Fodstad et al. |
| 6,315,940 B1 | 11/2001 | Nisch et al. |
| 6,344,326 B1 | 2/2002 | Nelson |
| 6,361,958 B1 | 3/2002 | Shieh |
| 6,368,871 B1 | 4/2002 | Christel et al. |
| 6,387,290 B1 | 5/2002 | Brody et al. |
| 6,406,903 B2 | 6/2002 | Bray et al. |
| 6,432,630 B1 | 8/2002 | Blankenstein |
| 6,454,938 B2 | 9/2002 | Moon et al. |
| 6,465,225 B1 | 10/2002 | Fuhr et al. |
| 6,468,346 B2 | 10/2002 | Arnowitz et al. |
| 6,533,903 B2 | 3/2003 | Hayward et al. |
| 6,540,895 B1 | 4/2003 | Spence et al. |
| 6,565,225 B2 | 5/2003 | Mabuchi et al. |
| 6,613,525 B2 | 9/2003 | Nelson et al. |
| 6,632,619 B1 | 10/2003 | Harrison et al. |
| 6,635,163 B1 | 10/2003 | Han et al. |
| 6,664,104 B2 | 12/2003 | Pourahmadi et al. |
| 6,685,841 B2 | 2/2004 | Lopez et al. |
| 6,744,038 B2 | 6/2004 | Wang et al. |
| 6,746,503 B1 | 6/2004 | Benett et al. |
| 6,762,059 B2 | 7/2004 | Chan et al. |
| 6,783,647 B2 | 8/2004 | Culbertson et al. |
| 6,784,420 B2 | 8/2004 | Wang et al. |
| 6,797,057 B1 | 9/2004 | Amos et al. |
| 6,802,489 B2 | 10/2004 | Marr et al. |
| 6,815,664 B2 | 11/2004 | Wang et al. |
| 6,830,936 B2 | 12/2004 | Anderson et al. |
| 6,833,542 B2 | 12/2004 | Wang et al. |
| 6,878,271 B2 | 4/2005 | Gilbert et al. |
| 6,881,315 B2 | 4/2005 | Iida et al. |
| 6,893,502 B2 | 5/2005 | Papadimitrakopoulos et al. |
| 6,893,881 B1 | 5/2005 | Fodstad et al. |
| 6,913,697 B2 | 7/2005 | Lopez et al. |
| 6,958,245 B2 | 10/2005 | Seul et al. |
| 6,991,939 B2 | 1/2006 | Walt et al. |
| 7,068,874 B2 | 6/2006 | Wang et al. |
| 7,088,455 B1 | 8/2006 | Kirkpatrick et al. |
| 7,150,812 B2 | 12/2006 | Huang et al. |
| 7,155,082 B2 | 12/2006 | Oakey et al. |
| 7,202,045 B2 | 4/2007 | Hanash et al. |
| 7,205,157 B2 | 4/2007 | Jurgensen et al. |
| 7,214,298 B2 | 5/2007 | Spence et al. |
| 7,214,348 B2 | 5/2007 | Desmond et al. |
| 7,241,988 B2 | 7/2007 | Gruber et al. |
| 7,276,170 B2 | 10/2007 | Oakey et al. |
| 7,294,503 B2 | 11/2007 | Quake et al. |
| 7,312,085 B2 | 12/2007 | Chou et al. |
| 7,318,902 B2 | 1/2008 | Oakey et al. |
| 7,435,568 B2 | 10/2008 | Kas et al. |
| 7,442,339 B2 | 10/2008 | Sundararajan et al. |
| 7,460,240 B2 | 12/2008 | Akcakir |
| 7,472,794 B2 | 1/2009 | Oakey et al. |
| 7,638,339 B2 | 12/2009 | Sundararajan et al. |
| 7,651,838 B2 | 1/2010 | Paterlini-Brechot |
| 7,713,705 B2 | 5/2010 | Buechler et al. |
| 7,745,788 B2 | 6/2010 | Appleyard et al. |
| 8,119,976 B2 | 2/2012 | Squier |
| 9,487,812 B2 | 11/2016 | Neeves et al. |
| 2002/0062783 A1 | 5/2002 | Bray |
| 2002/0108859 A1 | 8/2002 | Wang et al. |
| 2002/0113204 A1 | 8/2002 | Wang et al. |
| 2002/0115163 A1 | 8/2002 | Wang et al. |
| 2002/0123112 A1 | 9/2002 | Wang et al. |
| 2002/0172987 A1 | 11/2002 | Terstappen et al. |
| 2003/0024470 A1 | 2/2003 | Myerson |
| 2003/0072682 A1 | 4/2003 | Kikinis |
| 2003/0124516 A1 | 7/2003 | Chung et al. |
| 2004/0067167 A1 | 4/2004 | Zhang et al. |
| 2005/0175478 A1 | 8/2005 | Marr et al. |
| 2006/0060767 A1 | 3/2006 | Wang et al. |
| 2006/0142632 A1 | 6/2006 | Meretei |
| 2006/0171846 A1 | 8/2006 | Mar |
| 2007/0125941 A1 | 6/2007 | Lee et al. |
| 2008/0093306 A1 | 4/2008 | Oakey et al. |
| 2009/0062828 A1 | 3/2009 | Marr |
| 2009/0110010 A1 | 4/2009 | Squier |
| 2009/0188795 A1 | 7/2009 | Oakey et al. |
| 2009/0280518 A1 | 11/2009 | Adamo et al. |
| 2010/0203143 A1* | 8/2010 | Ingber ............... A61K 41/0052 424/489 |
| 2011/0270434 A1 | 11/2011 | Fischer et al. |
| 2012/0226093 A1* | 9/2012 | Creighton ............. H01F 7/0273 600/12 |
| 2013/0172728 A1* | 7/2013 | Gaitas ................ A61K 41/0052 600/411 |
| 2013/0183660 A1 | 7/2013 | Yu et al. |
| 2014/0366638 A1 | 12/2014 | Sawetski et al. |

FOREIGN PATENT DOCUMENTS

| | | |
|---|---|---|
| EP | 1412729 | 1/2003 |
| EP | 1438398 | 5/2003 |
| EP | 1338894 | 8/2003 |
| EP | 1485713 | 9/2003 |
| EP | 1499706 | 10/2003 |
| EP | 1539350 | 1/2004 |
| EP | 1529211 | 2/2004 |
| EP | 1542802 | 3/2004 |
| EP | 1418003 | 5/2004 |
| EP | 1462800 | 9/2004 |
| EP | 919812 | 10/2004 |
| WO | WO 94/29707 | 12/1994 |
| WO | WO 98/10267 | 3/1998 |

(56) References Cited

FOREIGN PATENT DOCUMENTS

| WO | WO 99/44064 | 9/1999 |
|----|-------------|--------|
| WO | WO 00/00816 | 1/2000 |
| WO | WO 02/12896 | 2/2002 |
| WO | WO 02/28523 | 4/2002 |
| WO | WO 02/30562 | 4/2002 |
| WO | WO 02/44689 | 6/2002 |
| WO | WO 03/031938 | 4/2003 |
| WO | WO 03/066191 | 8/2003 |
| WO | WO 2004/029221 | 4/2004 |
| WO | WO 2004/037374 | 5/2004 |
| WO | WO 2004/056978 | 7/2004 |

OTHER PUBLICATIONS

Applegate et al., "Microfluidic sorting system based on optical waveguide integration and diode laser bar trapping", Lab on a Chip, Jan. 20, 2006, vol. 6, pp. 422-426, The Royal Society of Chemistry.
Applegate et al., "Optical trapping, manipulation, and sorting of cells and colloids in microfluidic systems with diode laser bars", Colorado School of Mines, 2002, pp. 1-9.
Archer et al. "Cell Reactions to Dielectrophoretic Manipulation." Biochemical and Biophysical Research Communications. 1999;257:687-98.
Ashcroft et al., "Solid State Physics." Orlando, FL: Saunders College Publishing; 1976.
Ashkin et al. "Optical Trapping and Manipulation of Viruses and Bacteria," 1987, Science, vol. 235, pp. 1517-1520.
Author Unknown, "MicCell: Frequently Asked Questions", available at www.gesim.de, 2007, 4 pages.
Author Unknown, "The Optical Stretcher", available at http://www.uni/leipzig.de/~pwm/kas/os/os.html, cite updated on Nov. 23, 2005, 2 pages.
Babincova et al., "Selective treatment of neoplastic cells using ferritin-mediated electromagnetic hxgerthermia,"Medical Hypotheses, 2000, vol. 54(2), pp. 177-179.
Baldessari et al., "Two touching spherical drops in uniaxial extensional flow: Analytic solution to the creeping flow problem," 2005, Journal of Colloid and Interface Science, vol. 289, pp. 262-270.
Bauer, "Advances in cell separation: recent developments in counterflow centrifugal elutriation and continuous flow cell separation." Journal of Chromatography.1999;722:55-69.
Becker et al. "Fabrication of Microstructures With High Aspect Ratios and Great Structural heights by Synchrotron Radiation Lithography, Galvanoforming, and Plastic Moulding (LIGA Process)." Microelectronic Engineering. 1986;4:35-56.
Becker et al. "Planar quartz chips with submicron channels for two-dimensional capillary electrophoresis applications." J. Micromech Microeng.1998;9:24-28.
Beebe et al., "Functional Hydrogel Structures for Autonomous Flow Control Inside Microfluidic Channels", Nature, Apr. 6, 2000, pp. 588-590, 404, Nature Publishing Group (USA), a division of Macmillan Publishers Ltd., United Kingdom.
Benincasa et al. "Cell Sorting by One Gravity SPLITT Fractionation." Analytical Chemistry. 2005; 77(16):5294-5301.
Berg, "Random Walks in Biology." Princeton University Press. Princeton, NJ; 1993.
Brown et al. "Optical Waveguides Via Viscosity-Mismatched Microfluidic Flows." Department of Chemical Engineering, Colorado School of Mines. Applied Physics Letters 88, 134109 (2006).
Chan, et al., "DNA Mapping Using Microfluidic Stretching and Single-Molecule Detection of Flourescent Site-Specific Tags", Genome Research, 2004, vol. 14, pp. 1137-1146, Cold Spring Harbor Laboratory Press.
Chiu et al., "Patterned Deposition of Cells and Proteins Onto Surfaces by Using Three-Dimensional Microfluidic Systems", Proceedings of the National Academy of Sciences of the United States of America, Mar. 14, 2000, pp. 2408-2413, 97-#6, National Academy of Sciences, USA.

Chou et al., "A Microfabricated Device for Sizing and Sorting DNA Molecules", Proceedings of the National Academy of Sciences of the United States of America, Jan. 5, 1999, pp. 11-13, 96-#1, National Academy of Sciences, USA.
Chou et al., "Sorting by diffusion: An asymmetric obstacle course for continuous molecular separation." PNAS. 1999; 96(24):13762-13765.
Davies et al. "Optically Controlled Collisions of Biological Objects." SPIE Proceedings, Optical Investigations of Cells In Vitro and In Vivo, 15, Apr. 29, 1998, pp. 15-22.
De Kretser et al., "The Separation of Cell Populations using Monoclonal Antibodies attached to Sepharose." Tissue Antigens. 1980;16:317-325.
Delamarche et al., "Microfluidic Networks for Chemical Patterning of Substrates: Design and Application to Bioassays", Journal of the American Chemical Society, Jan. 9, 1998, pp. 500-508, 120, American Chemical Society, USA.
Delamarche et al., "Patterned Delivery of Immunoglobulins to Surfaces Using Microfluidic Networks", Science, May 2, 1997, pp. 779-781, 276, American Association for the Advancement of Science, USA.
Deshmukh et al., "Continuous Micromixer With Pulsatile Micropumps. Solid-State Sensor and Actuator Workshop." Hilton Head Island, South Carolina; Jun. 4-8, 2000:73-76.
Desprat, et al., "Creep Function of a Single Living Cell", Biophysical Journal, Mar. 2005, vol. 88, pp. 2224-2233, Biophysical Society.
Duffy et al., "Rapid Prototyping of Microfluidic Systems in Poly(dimethylsiloxane)", Anal. Chem., 70 (23) 4974-4984, 1998 (abstract only).
Eigen et al., "Sorting Single Molecules: Application to Diagnostics and Evolutionary Biotechnology", Proceedings of the National Academy of Sciences of the United States of America, Jun. 1994, pp. 5740-5747, 91, National Academy of Sciences, USA.
Evans et al., "The Bubble Spring and Channel (BSAC) Valve: An Actuated, Bi-Stable Mechanical Valve for In-Plane Fluid Control. Transducers '99." Sendai, Japan; Jun. 7-10, 1999.
Eyal et al., "Velocity-independent microfluidic flow cytometry", Electrophoresis, Aug. 2002;23(16):2653-7 (abstract only).
Farooqui et al. "Microfabrication of Submicron Nozzles in Silicon Nitride." Journal of Microelectromechanical Systems. 1992; 1(2):86-88.
Fiedler et al., "Dielectrophoretic Sorting of Particles and Cells in a Microsystem", Analytical Chemistry, May 1, 1998, pp. 1909-1915, 70-#9, American Chemical Society, USA.
Freemantle, "Downsizing Chemistry", Chemical & Engineering News, Feb. 22, 1999, pp. 27-39, 77-#8, American Chemical Society.
Fu et al., "A Microfabricated Flourescence-Activated Cell Sorter", Nature Biotechnology, Nov. 1999, pp. 1109-1111, 17, Nature America Inc., USA.
Fu et al., "An integrated miscrofabricated cell sorter." Analytical Chemistry. 2002;74(11):2451-2457.
Fuhr et al., "Biological Application of Microstructures", Topics in Current Chemistry, 1997, pp. 83-116, 194, Springer-Verlag, Germany.
Gambin et al. "Microfabricated Rubber Microscope Using Soft Solid Immersion Lenses." Department of Applied Physics, California Institute of Technology. Applied Physics Letters 88, 174102 (2006).
Gast, et al., "The development of integrated microfluidic systems at GeSiM", Lab on a Chip, 2003, vol. 3, pp. 6N-1 ON, The Royal Society of Chemistry.
Gast, et al., "The microscopy cell (MicCell), a versatile modular flowthrough system for cell biology, biomaterial research, and nanotechnology", Microfluid Nanofluid (2006), published on-line Jul. 27, 2005, vol. 2, pp. 21-36, Springer-Verlag.
Ghosh et al., "Controlled Propulsion of Artificial Magnetic Nanostructured Propellers," Nano Letters, 2009, vol. 9(6), pp. 2243-2245.
Giddings, "Chemistry 'Eddy' Diffusion in Chromatography." Nature. 1959;184:357-358.
Giddings, "Field-Flow Fractionation: Analysis of Macromolecular, Colloidal, and Particulate Materials." Science. 1993;260:1456-1465.

(56) References Cited

OTHER PUBLICATIONS

Giddings, "Unified Separation Science." John Wiley & Sons, Inc. 1991; Cover Page & Table of Contents only.

Gu, et al., "A single beam near-field laser trap for optical stretching, folding and rotation of erythrocytes", Optics Express, Feb. 6, 2007, vol. 15, No. 3., pp. 1369-1375, Optical Society of America.

Guck, et al., "Optical Deformability as an Inherent Cell Marker for Testing Malignant Transformation and Metastatic Competence", Biophysical Journal, May 2005, vol. 88, pp. 3689-3698, Biophysical Society.

Guck, et al., "The Optical Stretcher: A Novel Laser Tool to Micromanipulate Cells", Biophysical Journal, Aug. 2001, vol. 81, pp. 767-784, Biophysical Society.

Han et al., "Separation of Long DNA Molecules in a Microfabricated Entropic Trap Array." Science. 2000;288: 1026-1029.

Hartford, "Google's Next Frontier: Inside the Human Body," Nanotechnology, 2014, retrieved from http://www.mddionline.com/article/google%E2%80%99s-next-frontier-inside-human-body-Oct. 28, 2014.

Huang et al., "A DNA prism for high-speed continuous fractionation of large DNA molecules." Nature Biotechnology. 2002;20:1048-1051.

Huang et al., "Electric Manipulation of Bioparticles and Macromoledules on Microfabricated Electrodes", Analytical Chemistry, Apr. 1, 2001, pp. 1549-1559, 73-#7, American Chemical Society, USA.

Huang et al., "Role of Molecular Size in Ratchet Fractionation." 2002; 89(17):178301-1-178301-4.

Huh et al., "Gravity-driven microhydrodynamics-based cell sorter (microHYCS) for rapid, inexpensive, and efficient cell separation and size-profiling." 2nd Annual International IEEE-EMBS Special Topic Conference on Microtechnology in Medicine and Biology. Madison, Wisconsin USA; May 2-4, 2002:466-469.

Jeon et al., "Generation of Solution and Surface Gradients using Microfluidic Systems", Langmuir, 2000, pp. 8311-8316, 16-#22, American Chemical Society, USA.

Kamholz et al., "Quantitative Analysis of Molecular Interaction in a Microfluidic Channel: the T-Sensor", Analytical Chemistry, Dec. 1, 1999, pp. 5340-5347, 71-#23, American Chemical Society, USA.

Kenis et al., "Microfabrication Inside Capillaries Using Multiphase Laminar Flow Patterning", Science, Jul. 2, 1999, pp. 83-85, 285, American Association for the Advancement of Science, USA.

Kim et al. Polymer microstructures formed by moulding in capillaries. Nature. 1995;376:581-584.

Kim, et al., "Stretching and immobilization of DNA for studies of protein—DNA interactions at the single-molecule level", Nano Review, Apr. 18, 2007, Nanoscale Res Letter vol. 2, pp. 185-201, Springer.

Kumar et al. Cell Separation: A Review. Pathology. 1984;16:53-62.

Lang, et al., "Resource Letter: LBOT-1: Letter based optical tweezers", Am J Phys., Mar. 2003, vol. 71(3), pp. 201-215, National Institute of Health.

Lanza et al., "Magnetic resonance molecular imaging with nanoparticles," Joural of Nuclear Cardiology, 2004, vol. 11(6), pp. 733-743.

Li et al, "Transport, Manipulation, and Reaction of Biological Cells On-Chip Using Electrokinetic Effects", Analytical Chemistry, Apr. 15, 1997, pp. 1564-1568, 69-#8, American Chemical Society, USA.

Lim, et al., "Large deformation of living cells using laser traps", Acta Materialia, Apr. 19, 2004, vol. 52, Issue 7, pp. 1837-1845, Elsevier Science Ltd., (Only abstract and figures/tables provided, 6 pages).

Lincoln et al., "High-Throughput Rheological Measurements with an Optical Stretcher", Methods in Cell Biology, vol. 83, 2007, pages 397-423 (abstract only).

Lincoln, et al., "Deformability-Based Flow Cytometry", Wiley InterScience, May 17, 2004, Cytometry Part A 59A, pp. 203-209, Wiley-Liss, Inc.

Lu, et al., "Viscoelastic properties of individual glial cells and neurons in the CNS", PNAS, Nov. 21, 2006, vol. 103, No. 47, pp. 17759-17764, The National Academy of Sciences of the USA.

Lumsdon et al. "Two-Dimensional Crystallization of Microspheres by a Coplanar AC Electric Field," 2004, Langmuir, vol. 20, pp. 2108-2116.

Martin et al., "Feeling with light for cancer", 2006, Progress in biomedical optics and imaging, vol. 7 (abstract only).

McClain et al., "Flow Cytometry of *Escherichia coli* on Microfluidic Devices", Anal. Chem., 73 (21), 5334-5338, 2001 (abstract only).

Mehrishi et al. "Electrophoresis of cells and the biological relevance of surface charge." Electrophoresis. 2002;23:1984-1994.

MicCell™ Parts List, GeSiM, www.gesim.de, 2007, 2 pages.

MicCell™ Special Designs (Selection), GeSiM, www.gesim.de, date unknown, 2 pages.

Moore et al. Lymphocyte fractionation using immunomagnetic colloid and a dipole magnet flow cell sorter. J Biochem Biophys Methods. 1998;37:11-33.

Néron, "Fiber Coupling Efficiency Calculation," Doric Lenses, 2007, 7 pages.

Oakey et al., "Laminar Flow-Based Separations at the Microscale", Biotechnology Progress, Sep. 24, 2002, pp. 1439-1442, 18-#6, American Chemical Society and the American Institute of Chemical Engineers, USA.

Olson et al., "An in Situ Flow Cytometer for the Optical Analysis of Individual Particles in Seawater", found at http://www.whoi.edu/science/B/Olsonlab/insitu2001.htm, publication date unknown.

Pak et al., "High-speed propulsion of flexible nanowire motors: Theory and experiments," Soft Matter 7.18, 2011, vol. 7, pp. 8169-8181.

Pamme et al., "Counting and sizing of particles and particle agglomerates in a microfluidic device using laser light scattering: application to a particle-enhanced immunoassay", Lap Chip, 2003, 3, 187-192.

Product literature for GEM, A system for blood testing: "GEM PCL Step by Step Guide" and "GEM Premier 3000", publication date unknown.

Raymond et al. "Continuous Separation of High Molecular Weight Compounds using a Microliter Volume Free-Flow Electrophoresis Microstructure." 1996;68:2515-2522.

Reed et al., "High throughput call nanomechanics with mechanical imaging interferometry", 2008 Nanotechnology 19. 235101 (8 pages) (abstract only).

Sawetzki et al., "In situ assembly of linked geometrically coupled microdevices," PNAS, 2008, vol. 105(51), pp. 20141-20145.

Sawetzki et al., "Viscoelasticity as a Biomarker for High-Throughput Flow Cytometry," 2013, Biophysical Journal, vol. 105(10), pp. 2281-2288.

Sery et al., "Compact laser tweezers," 2007, Proc. SPIE 6609, 15th Czech-Polish-Slovak Conference on Wave and Quantum Aspects of Contemporary Optics, 66090N, 2 pages (abstract only).

Singh, et al., "A Miniaturized Wide-Angle 2D Cytometer", Wiley InterScience, Feb. 23, 2006, Cytometry Part A 69A, pp. 307-315, International Society for Analytical Cytology.

Sraj et al. "Cell deformation cytometry using diode-bar optical stretchers," Journal of Biomedical Optics, Jul./Aug. 2010, vol. 15, No. 4, 7 pages.

Takayama et al. "Patterning Cells and Their Environments Using Multiple Laminar Fluid Flows in Capillary Networks", Proceedings of the National Academy of Sciences of the United States of America, May 11, 1999, pp. 5545-5548, 96-#10, national Academy of Sciences, USA.

Takayama et al. "Subcellular Position of Small Molecules", Nature, Jun. 28, 2001, p. 1016, 411, Nature Publishing Group (USA), a division of Macmillan Publishers Ltd., United Kingdom.

Tasci et al., "Surface-enabled propulsion and control of colloidal microwheels," Nature Communications, 2016, 6 pages.

Terray et al., "Microfluidic Control Using Colloidal Devices", Science, 2002, vol. 296, pp. 1841-1844.

Tong et al. Low Temperature Wafer Direct Bonding. Journal of Microelectromechanical Systems. 1994;3:29-35.

Turner et al. Confinement-Induced Entropic Recoil of Single DNA Molecules in a Nanofluidic Structure. Physical Review Letters. 2002;88:128103.1-128103.4.

(56) References Cited

OTHER PUBLICATIONS

Vezenov et al. "Integrated Fluorescent Light Source for Optofluidic Applications." Department of Chemistry and Chemical Biology, Harvard University. Applied Physics Letters 86, 041104 (2005).
Visscher, et al., "Single Beam Optical Trapping Integrated in a Confocal Microscope for Biological Applications", Cytometry, Apr. 10, 1991, vol. 12, pp. 485-491, Wiley-Liss, Inc.
Voldman et al. Holding Forces of Single-Particle Dielectrophoretic Traps. Biophysical Journal.2001;80:531-541.
Volkmuth et al. DNA electrophoresis in microlithographic arrays. Letters to Nature (1992) vol. 358; p. 600.
Weigl et al., "Microfluidic Diffusion-Based Separation and Detection", Science, Jan. 15, 1999, pp. 346-347, 283-#5400, American Association for the Advancement of Science, USA.
Wolfe et al. "Dynamic Control of Liquid-Core/Liquid-Cladding Optical Waveguides." Department of Chemistry and Chemical Biology. Harvard University. Aug. 24, 2004, vol. 101, No. 34. pp. 12434-12438.
Wuite, et al., "An Integrated Laser Trap/Flow Control Video Microscope for the Study of Single Biomolecules", Biophysical Journal, Aug. 2000, vol. 29, pp. 1155-1167, Biophysical Society.
Xu et al. Dielectrophoresis of human red cells in microchips. Electrophoresis. 1999;20:1829-1831.
Zhang et al. High-speed free-flow electrophoresis on chip. Anal Chem. 2003;75:5759-5766.
Zhang et al., "Characterizing the Swimming Properties of Artificial Bacterial Flagella," Nano Letters, 2009, vol. 9(10), pp. 3663-3667.
Official Action for U.S. Appl. No. 10/838,908, dated Feb. 24, 2006.
Official Action for U.S. Appl. No. 10/838,908, dated Oct. 30, 2006.
Official Action for U.S. Appl. No. 10/838,908, dated Oct. 4, 2007.
Official Action for U.S. Appl. No. 10/838,908, dated May 1, 2008, 2007.
Official Action for U.S. Appl. No. 10/838,908, dated Mar. 4, 2009.
Notice of Allowance for U.S. Appl. No. 10/838,908, dated Dec. 1, 2009.
Official Action for U.S. Appl. No. 11/329,491, dated Mar. 23, 2009.
Official Action for U.S. Appl. No. 11/329,491, dated Jun. 16, 2009.
Official Action for U.S. Appl. No. 11/329,491, dated Jun. 3, 2010.
Official Action for U.S. Appl. No. 11/329,491, dated Feb. 2, 2011.
Official Action for U.S. Appl. No. 11/329,491, dated Jul. 19, 2011 11 pages.
Official Action for U.S. Appl. No. 11/960,457, dated Jun. 18, 2008.
Official Action for U.S. Appl. No. 11/960,457, dated Jun. 25, 2008.
Official Action for U.S. Appl. No. 12/315,183, dated Jan. 14, 2010.
Official Action for U.S. Appl. No. 12/167,136, dated Nov. 10, 2010.
Official Action for U.S. Appl. No. 12/167,136, dated May 16, 2011 8 pages.
Official Action for U.S. Appl. No. 12/203,744, dated Mar. 29, 2011 6 pages (Restriction Requirement).
Official Action for U.S. Appl. No. 12/203,744, dated May 10, 2011 7 pages.
Official Action for U.S. Appl. No. 12/203,744, dated Dec. 28, 2011 9 pages.
Official Action for U.S. Appl. No. 12/239,449, dated Sep. 2, 2010 (Restriction Requirement).
Official Action for U.S. Appl. No. 12/239,449, dated Jan. 5, 2011.
Official Action for U.S. Appl. No. 12/239,449, dated May 18, 2011 9 pages.
Official Action for U.S. Appl. No. 12/239,449, dated May 1, 2014 8 pages.
Official Action for U.S. Appl. No. 12/239,449, dated Jan. 2, 2015 9 pages.
Examiner's Answer for U.S. Appl. No. 12/239,449, dated Sep. 25, 2015 8 pages.
Official Action for U.S. Appl. No. 13/770,875, dated Sep. 4, 2014, 12 pages.
Official Action for U.S. Appl. No. 13/770,875, dated Apr. 20, 2015 10 pages.
Official Action for U.S. Appl. No. 13/770,875, dated Oct. 28, 2015 10 pages.
Official Action for U.S. Appl. No. 13/770,875, dated Feb. 9, 2016, 11 pages.
Notice of Allowance for U.S. Appl. No. 13/770,875, dated Jul. 7, 2016, 12 pages.
Official Action for U.S. Appl. No. 14/307,269, dated Dec. 15, 2015, 10 pages.
Final Action for U.S. Appl. No. 14/307,269, dated Aug. 8, 2016, 10 pages.
Advisory Action for U.S. Appl. No. 14/307,269, dated Dec. 7, 2016, 3 pages.
Official Action for U.S. Appl. No. 14/307,269, dated Mar. 1, 2017, 10 pages.
Notice of Allowance for U.S. Appl. No. 14/307,269 dated Sep. 6, 2017, 7 pages.
Notice of Allowance for U.S. Appl. No. 12/239,449, dated Sep. 20, 2017 5 pages.
U.S. Appl. No. 11/329,492, filed Jan. 10, 2006.
U.S. Appl. No. 10/248,653, filed Feb. 4, 2003, now U.S. Pat. No. 7,318,902.
U.S. Appl. No. 11/395,691, filed Mar. 30, 2006, now U.S. Pat. No. 7,276,170.
U.S. Appl. No. 11/674,979, filed Feb. 14, 2007, now U.S. Pat. No. 7,472,794.
U.S. Appl. No. 11/960,457, filed Dec. 19, 2007.
U.S. Appl. No. 12/315,183, filed Nov. 25, 2008.
U.S. Appl. No. 12/167,136, filed Jul. 2, 2008, now U.S. Pat. No. 8,119,976.
U.S. Appl. No. 12/203,744, filed Sep. 3, 2008.
U.S. Appl. No. 12/239,449, filed Sep. 26, 2008.
U.S. Appl. No. 13/770,875, filed Feb. 19, 2003, now U.S. Pat. No. 9,487,812.
U.S. Appl. No. 14/307,269, filed Jun. 17, 2014.

\* cited by examiner

MAGNETIC-FIELD DRIVEN COLLOIDAL MICROBOTS, METHODS FOR FORMING AND USING THE SAME

CROSS REFERENCE TO RELATED APPLICATIONS

This application claims priority under 35 U.S.C. § 119(e) to U.S. Provisional Patent Application Ser. No. 62/132,682 filed on Mar. 13, 2015, which is incorporated herein in its entirety by reference. This application is also related to U.S. patent application Ser. No. 12/203,744 entitled Magnetic Field-Based Colloidal Atherectomy, filed on Sep. 3, 208, published as U.S. Publication No. 2009/0062828 on Mar. 5, 2009, which took priority to U.S. Provisional Patent Application No. 60/969,839, filed on Sep. 4, 2007. Each of these references are incorporated by reference in their entirety.

GOVERNMENT LICENSE RIGHTS

This invention was made with government support under grant number R21NS082933 awarded by the National Institutes of Health. The Government has certain rights in the invention.

FIELD OF THE INVENTION

The invention relates to a magnetic-field driven colloidal microbot, method of forming the microbot and a method of using the microbot.

BACKGROUND

Interventional cardiology is expensive, sometimes dangerous, but ultimately reasonably effective at saving lives with 600,000 angioplasties per year in the US alone, at a cost of about $12 billion. With such widespread use, approaches that make this less invasive and less expensive would not only allow faster recovery, it could lower our ever-increasing national health care costs.

Viscous forces plays a dominant role at small length scales. Locomotion by microbots is hindered because familiar (macroscopic) swimming mechanisms are ineffective against these forces. In other words, movement at this micrometer length scale is akin to doing the backstroke in honey. Microorganisms overcome these limitations through physical adaptations, like rotating flagellum, that are difficult to artificially replicate and control.

Many interventional procedures in the cardiovascular system require invasive catheter-based methods (e.g. diagnostic angiography, angioplasty) to reach their intended targets. These systems are problematic because catheters cannot access the entire vascular system. Moreover, they are an inelegant approach to applications that require finesse, such as removing a blood clot without damaging the vessel wall. Because of the inherent advantages associated with a non-invasive approach for medical applications, magnetic field techniques have been used extensively to drive and direct microbots. These previous efforts are limited in their ability to control direction and continuously power the smaller devices.

U.S. Patent Publication No. 2006/0142632 to Meretei entitled "Systems and methods for removing plaque from a blood vessel" is incorporated by reference in its entirety. Meretei describes a system and method for removing accumulated plaque in a blood vessel using ferrofluids that are introduced to the bloodstream of a patent. The ferrofluids are magnetically manipulated and moved throughout the blood vessels of the patent with an external magnetic field generator to break up and remove accumulated plaque. U.S. Patent Publication No. 2009/0062828 to Marr entitled "Magnetic Field-Based Colloidal Atherectomy," is incorporated by reference in its entirety. Marr describes methods, devices and systems for performing a non-invasive form of angioplasty using colloidal particles that can be magnetically controlled. Marr described the idea of rotating colloidal assemblies as biomedical microtools. Zhang, Li, et al. "Characterizing the swimming properties of artificial bacterial flagella" Nano Letters 9.10 (2009): 3663-3667, is incorporated by reference in its entirety. Zhang describes artificial bacterial flagella (ABF) consisting of helical tails similar to natural flagella comprising soft-magnetic heads. The ABFs are controlled wirelessly using a low rotating magnetic field. Ghosh, Ambarish, and Peer Fischer. "Controlled propulsion of artificial magnetic nanostructured propellers" Nano letters 9.6 (2009): 2243-2245 is incorporated by reference. Pak, On Shun, et al. "High-speed propulsion of flexible nanowire motors: Theory and experiments." Soft Matter 7.18 (2011): 8169-8181, is incorporated by reference in its entirety. Pak describes a high-speed fuel-free magnetically-driven propeller for use in a biological environment.

Thus, there is a need for an improved mechanism and method to improve interventional procedures in biological systems. The present invention overcomes these and other issues.

SUMMARY

The present invention provides a novel approach to assemble, target, and disassemble microbots in biological systems, such as the vasculature system, that can replace and improve current invasive procedures. Though the invention can be used with multiple biological systems, the cardiovascular system is discussed in detail. One skilled in the art would understand how the invention can be used in other biological applications.

This novel approach uses a combination of oscillating magnetic fields to create wheel-shaped colloidal assemblies that roll along or propels itself on available surfaces (which are plentiful within the human vascular system). As a result, this device and method can be used to generate and control "microbots" that can translate throughout the body about 10-100 times faster than competing approaches that rely on devices that swim through fluid (blood).

In the present invention, micrometer sized magnetic (paramagnetic or superparamagnetic) particles, or colloids, are assembled into microbots, which can be rotated and propelled along a surface using external magnetic fields. The microbots can be any suitable shape, including disc shaped.

The present invention differs from other prior art methods. Unlike Meretei, the present invention assemblies particles into microbots. Meretei simply discloses a ferrofluid movement. The propulsion method of the microbot of the present invention also differs from the propulsion method discussed in Meretei. In the present invention, the propulsion relies on rolling along a surface instead of other methods like magnetophoresis. The rolling propulsion method of the invention is therefore able to be orders of magnitude faster than other methods.

With properly configured dynamic fields, these microbots "stand up" along the surface and translocate by rolling along the cells that line blood vessels. The microbots provide enhanced traction, first through physical modification (i.e. shaping the microbots) and can include chemical modification (i.e. making the microbots sticky/tacky) to significantly increase the translation speeds of the microbots. Advantageously, the microbots are fast and can achieve a speed of greater than about 1 mm/s, which can be necessary for many practical application. Another advantage of the present invention is that as the microbots move along surfaces, they translate in low velocity regions of arterial flow allowing them to move "upstream." For example, some prior art methods rely on blood flow to deliver a device to a specific location in a patient. The surface of the device can be treated to create an affinity for a specific target in the patient. However, in the case of an ischemic stroke, there is no blood flow for a device to rely upon to reach the clot. Thus, prior art methods are not able to reach the clot because of the lack of blood flow. The present invention does not rely on blood flow or flow of any medium. Thus, the device is able to reach locations in the patient that could not be reached with prior art methods or devices and remove the clot and/or deliver medications. Furthermore, the translation velocity of the present invention is greater than other prior art methods. Finally, their translation direction can be tightly controlled allowing for targeted applications within the biological system of an animal or human.

Based on previous investigations, microscale particles can be readily assembled into pumps, valves and mixers (Terray, et al., Microfluidic Control Using Colloidal Devices, Science, 296, 1841 (2002) and Sawetzki et al., In Situ Assembly of Liked Geometrically Coupled Microdevices, PNAS, 150, 20141-45 (2008) (each of which are incorporated by reference in their entirety)). The colloidal, bead-based systems can be employed in healthcare to target diseased tissues in a minimally invasive manner.

A microbot is an assembly of colloidal particles (though a single colloidal particle can be use) in the presence of a magnetic field and disintegrates back to colloidal particles once the magnetic field is removed. The microbot can move by rolling along a surface. Microbots can perform a variety of functions in biological systems, including for example the cardiovascular system. In some embodiments, the colloidal particles can be injected and assembled in-situ to form the microbots. The advantages of this method are based on three traits. First, the size of the microbots allow for them to be used in systems as small as the size of blood cells. As individual particles, they can be injected into and pass within the vasculature. Second, these particles can be assembled and manipulated with applied external electromagnetic fields. Assemblies quickly dissociate into individual particles in the absence of a field. These traits are complemented by low toxicity and other advantages that have led to their current use in medical applications. For example, in vascular systems, the individual particles can be removed by macrophage by phagocytosis. Third, given the enhanced magnetic contrast associated with these systems, it is possible to monitor the procedure, in vivo, via magnetic resonance imaging or angiography.

The microbots of the present invention are powered and controlled with readily-tunable and dynamic applied external magnetic fields, which is more controllable and particularly appropriate for the vascular system where available surfaces are bountiful. Because the method converts rotational energy to translational energy using wall friction, assemblies move significantly faster (~100 µm/s) than other propulsion strategies that rely of friction with surrounding liquids (1-10 µm/s). The present invention enables applications that require rapid complex movement or transport over macroscopic distances. When the external field is removed, devices immediately disassemble into individual colloids.

Speeds of the microbots using the present invention are significantly faster than many artificial and even the normal biological systems of human beings and animals. Experiments of assemblies on rigid glass slides show significant "slip" in the microbot translation. On rigid surfaces, device efficiencies of less than about 10% are observed; however potential velocities>1 mm/s enable significant application as travel over macroscopic distances can occur within clinical timeframes. Research from the tire industry indicates that the mechanical properties of the surface can have a significant impact on rolling resistance. As the microbots translate upon soft endothelial cell surfaces, rolling resistance increases and significantly speeds up translation. To further increase translation speeds, "tires" of increased elasticity can be created by coating colloids with gels commonly used for in vivo applications to improve biocompatibility and delay phagocytosis. To enhance targeting, ligands for receptors expressed on endothelial cells at injury/infection sites can be conjugated to the microbots.

An aspect of the invention is a microbot for use in a biological system. The microbot includes at least one colloidal particle which has magnetic properties. The colloidal particles are activated when a magnetic field is applied to the colloidal particle to form a microbot.

An aspect of the invention is a method to form a microbot. The method includes applying a magnetic field to at least one colloidal particle, wherein the colloidal particle forms a microbot in a biological system of a patient in the presence of the magnetic field. The microbot disintegrates when the magnetic field is removed.

An aspect of the invention is a method for using a microbot in a biological system to treat a patient. The method includes inserting at least one particle in the biological system of the patient. A magnetic field is applied to the particle to form the microbot. The microbot is directed to a predetermined location in the biological system of the patient by translating the microbot on a surface in the biological system.

An aspect of the invention is a device to apply a magnetic field to form a microbot, and move a microbot on a surface. The magnetic field can be created by applying a current or charge through a conductive material (for example copper). The magnetic field can be controlled in three dimensions (i.e. x, y, and z). The device can be any suitable size. One or more magnet can also be used to produce a magnetic field.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
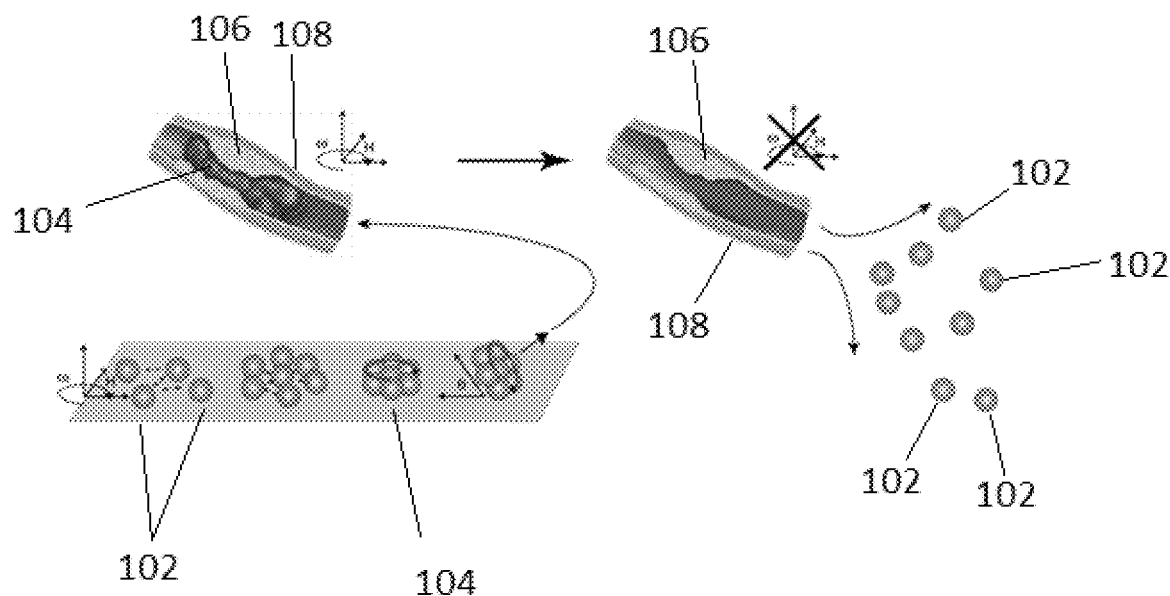
FIG. 1 illustrates an example application where an external magnetic field is used to assemble microbots, then used for a blood clot removal in a blood vessel.

The present invention relates to a precise and controllable device and method suitable for exploring the body of a patient, delivering medication to a location in a patient, or treating a patient (for example by removing or reducing an occlusion in a patient) that moves in a system by rolling on surfaces. This mechanism can be used to translate microbots at speeds that are an order-of-magnitude greater than other propulsion mechanisms in similarly sized bots. The advantages of this approach include; (i) the microbots are fast and could achieve about 1 mm/s speeds necessary for practical application, (ii) by moving along surfaces the microbots translate in low velocity regions of arterial flow allowing the microbots to move "upstream", and (iii) the microbots translation direction can be tightly controlled allowing for targeted applications.

An aspect of the invention is a microbot for use in a biological system. The microbot includes at least one colloidal particle, which is paramagnetic or superparamagnetic. The colloidal particles are activated when a magnetic field is applied to the colloidal particles to form the microbot.

The colloidal particle can be any suitable magnetic material including, but not limited to, iron oxide, iron or iron containing compounds, magnesium or magnesium containing compounds, molybdenum or molybdenum containing compounds, lithium or lithium containing compounds, tantalum or tantalum containing compounds, sodium or sodium containing compounds, aluminum or aluminum containing compounds, calcium or calcium containing compounds, titanium or titanium containing compounds, manganese or manganese containing compounds, strontium or strontium containing compounds, zirconium or zirconium containing compounds, ruthenium or ruthenium containing compounds, rhodium or rhodium containing compounds, palladium or palladium containing compounds, tin or tin containing compounds, barium or barium containing compounds, cerium or cerium containing compounds, neodymium or neodymium containing compounds, samarium or samarium containing compounds, europium or europium containing compounds, terbium or terbium containing compounds, dysprosium or dysprosium containing compounds, holmium or holmium containing compounds, erbium or erbium containing compounds, thulium or thulium containing compounds, tungsten or tungsten containing compounds, osmium or osmium containing compounds, iridium or iridium containing compounds, platinum or platinum containing compounds, or any other paramagnetic or superparamagnetic material. The materials of the colloidal particles allow for the microbot to disassemble to the colloidal particles once the magnetic field is removed. In other words, the materials of the colloidal particles do not produce a microbot that cannot be disassembled. The material can be a non-magnetic material that is later coated, doped, implanted with a material, or otherwise manipulated to become magnetic. For example, the material can be polystyrene doped with iron oxide. Other suitable materials include Dynabeads® (polystyrene doped with iron oxide) available from ThermoFischer Scientific. In some embodiments, the colloidal particles are approved for use within a patient. In some embodiments, the material can be biodegradable such as polylactic acid. In some embodiments, the material of the colloidal particles can have a hardness of less or equal to or greater than polystyrene, when measured in accordance with ASTM E18 or similar method. The colloidal particles can contain a therapeutic material. The therapeutic material can be imbedded into the colloidal particle and slowly released from the colloidal particle as the particle breaks down. In some embodiments, the material of the microbots can be used to provide radiation therapy to a location within the patient. For example, the magnetic field can be altered to heat the particles of the microbot causing localized hyperthermia.

The colloidal particles can be coated. Suitable coating materials include, but are not limited to an antimicrobial material, an antiplatelet material, a fibrinolytic material, a tactifying material, an antibacterial material, a cancer therapeutic, at least one ligand and combinations thereof. Suitable antimicrobial materials include but are not limited to silver containing compounds, lincosamides (for example clindamycin), tetracyclines (for example doxycline or minocycline), fluoroquinolones (for example ciprofloxacin, oflozacin, levofloxacin or norfloxacin), aminoglycosides (for example streptomycin, tobramycin, gentamycin, or amikacin), and other antimicrobial materials. Suitable antiplatelet or anticoagulation materials include, but are not limited to, dextran, abciximab, clopidogrel, aspirin or other suitable antiplatelet materials. Suitable fibrinolytic materials include, but are not limited to, tissue plasminogen activator, plasmin, urokinase plasminogen activator or other fibrinolytic materials. Suitable tactifying materials include, but are not limited to, hydrophilic and hydrophobic, positively or negative charged or uncharged, moieties to enhance interaction with surface. Suitable antibacterial materials include, but are not limited to, surfactants, rifampin, chlorhexidine, sulfadiazine, erythromycin, or other antibacterial materials. In some embodiments, ligands for receptors expressed on the endothelial cells can be conjugated to the microbots. Suitable ligands include, but are not limited to, selectins, fibrinogen. The ligands can be conjugated to the microbot by physical adsorption or covalent coupling. Chemotherapy materials can be used to provide localized chemotherapy to a patient. One skilled in the art would understand that they type of cancer therapeutic material provided to the patient will depend upon multiple factors, including the type of cancer, the biology of the cancer and the biology of the patient. Thus, while an exhaustive list is not included, one skilled in the art would understand that any conjugated medicine can be used. The colloidal particles can also include a material or coating, or be treated, to change the charge associated with the surface. By way of example, the charge of the microbot can be treated to make it anionic, cationic or neutral.

The surface of the colloidal particles, and thereby the microbot, can be smooth. In some embodiments, the surface of the colloidal particles can be decorated with other materials to increase the surface area of the microbot, thereby increasing traction of the microbot. The decoration materials can be adhered to the surface of the colloidal particles. In some embodiments, the decoration materials can have smaller dimensions from the dimension of the colloidal particle that it covers. The surface of the colloidal particles can also be manipulated during the formation of the particles to increase the surface area. For example, the surface of a colloidal particle can be adjusted by changing the synthesis of the particle. The surface of the colloidal particles can also be removed to roughen the surface by chemical etching or by surface roughening (e.g. abrasive blasting, or particle on particle roughening).

A single colloidal particle can form a microbot, but in some embodiments, at least two colloidal particles are joined together to make the microbot. The number of colloidal particles will depend upon the application of the microbots. While there is no maximum limit on the number of colloidal particles used to form a microbot, in some embodiments, between 1 to about 500 colloidal particles are joined to make the microbots. In some embodiments, three colloidal particles are joined to make the microbot. Multiple colloidal particles of the same size or of different sizes can be used to form a microbot. The dimensions of the microbot can dependent upon the number and size of the colloidal particles used. The dimensions of the colloidal particles are limited by the use of the microbots. For example, if the microbot will be used in a vascular system of a patient, the dimensions of the colloidal particles are limited by the dimension of the vein or artery along which the microbot travels. The diameter of the colloidal particles can be between about 1 µm to about 4 µm. In some embodiments, the diameter of the colloidal particles can be between about 10 nm to 10 µm. In some embodiments, the microbot can have a diameter between about 10 nm and about 10 mm. The thickness of the microbot can be between about 10 nm and about 10 µm.

The magnetic fields can have a magnitude between about 1 mT to about 20 mT, however fields outside that range can also be effective. The magnitude can be local to the colloidal particles. One skilled in the art would understand that the magnetic field is dictated by the susceptibility of the colloidal particles. Thus, if a colloidal particle is receptive to a magnetic field, then a lower magnetic field can be used, while if the colloidal particle is not receptive to the magnetic field, then a higher magnetic field should be used. The magnetic field can be used to form, power and direct the microbot. The microbots form quickly after the magnetic field is applied, in some embodiments in less than about 20 seconds. In some embodiments, the microbot forms in between about 0.1 second to about 20 seconds. Furthermore, the colloidal particles can closely pack together (similar to a hexagonal crystalline structure) once the magnetic field is applied. Once the magnetic field is applied to the colloidal particles to form the microbot, the microbot can move (i.e. translating along the surface) at a rolling or translation velocity (V) of between about 1 µm/s and about 1 mm/s. In some embodiments, the microbot can move at a speed greater than about 1 mm/s. The microbot can be moved using a propulsion system. In some embodiments, the propulsion system can be a wall-based propulsion system. The microbot can advance through the patient at a camber angle relative to the wall or tissue, theta. Theta can be between about 0° (i.e. upright orientation compared to the surface) and 90° (i.e. laying flat on the surface). Notably, the microbot can roll along a surface regardless of the camber angle. However, larger camber angles allow the microbots to roll on round surfaces, such as the inner surface of a tube or vessel. The angle for theta can be set using the magnetic field, understanding that the camber angle can change as the microbot travels along a surface that changes (i.e. bumps, turns, etc.). The microbot can apply a force to the surface which it travels on of between about 250 fN to about 25 pN. The coefficient of friction as the microbot is moving within the patient can be between zero and unity.

Important parameters influencing the rolling velocity (V) include the number of particles comprising the microbot (n), its angular frequency ($\omega$), and, as the mirobot rotates, the outer circumferential velocity Vo>$\omega$R.

The microbot can rotate between about 1 hertz and about 100 hertz ($\omega$). Thus, the microbot can be used to remove material with rotational advancement of the microbot.

The magnetic field can be applied using any suitable device. By way of example only, the device can be large, similar to a CT or MM. In some embodiments, the microbot can be observed in situ using a MRI or other magnetic imaging device. Magnets within these devices can be used to control the microbots. In some embodiments, the magnetic field device can be small, such that it can be used in remote areas or for ease of use. A plurality of electromagnetic coils can be used to apply a magnetic field. The phase angle, $\varphi$, of the field applied to the microbot can be controlled by a user, for example with a device similar to a joystick, or directional keys. Application of the magnetic field can also direct the microbot. Thus, the magnetic field can control the rotational speed, the advancing speed, the angle relative to the wall, theta and the direction of the microbot. Once the magnetic field is removed from the microbots, they can return to the colloidal particle form, and can be absorbed or broken down by macrophages in the patient.

An aspect of the invention is a method to form a microbot. The method includes applying a magnetic field to at least one colloidal particle. The colloidal particles form the microbot in the presence of the magnetic field. In the absence of the magnetic field, the colloidal particles do not form a microbot.

The colloidal particle can be any suitable magnetic material including, but not limited to, iron oxide, iron or iron containing compounds, magnesium or magnesium containing compounds, molybdenum or molybdenum containing compounds, lithium or lithium containing compounds, tantalum or tantalum containing compounds, sodium or sodium containing compounds, aluminum or aluminum containing compounds, calcium or calcium containing compounds, titanium or titanium containing compounds, manganese or manganese containing compounds, strontium or strontium containing compounds, zirconium or zirconium containing compounds, ruthenium or ruthenium containing compounds, rhodium or rhodium containing compounds, palladium or palladium containing compounds, tin or tin containing compounds, barium or barium containing compounds, cerium or cerium containing compounds, neodymium or neodymium containing compounds, samarium or samarium containing compounds, europium or europium containing compounds, terbium or terbium containing compounds, dysprosium or dysprosium containing compounds, holmium or holmium containing compounds, erbium or erbium containing compounds, thulium or thulium containing compounds, tungsten or tungsten containing compounds, osmium or osmium containing compounds, iridium or iridium containing compounds, platinum or platinum containing compounds, or any other paramagnetic or superparamagnetic material. The materials of the colloidal particles allow for the microbot to disassemble to the colloidal particles once the magnetic field is removed. In other words, the materials of the colloidal particles do not produce a microbot that cannot be disassembled. The material can be a non-magnetic material that is later coated, doped, implanted with a material, or otherwise manipulated to become magnetic. For example, the material can be polystyrene doped with iron oxide. Other suitable materials include Dynabeads® available from ThermoFischer Scientific. In some embodiments, the colloidal particles are approved for use within a patient. In some embodiments, the material can be biodegradable such as polylactic acid. In some embodiments, the material of the colloidal particles can have a hardness of less or equal to or greater than polystyrene, when measured in accordance with ASTM E18 or similar method. The colloidal particles can contain a therapeutic material. The therapeutic material can be imbedded into the colloidal particle and slowly released from the colloidal particle as the particle breaks down. In some embodiments, the material of the microbots can be used to provide radiation therapy to a location within the patient. For example, the magnetic field can be altered to heat the particles of the microbot causing localized hyperthermia.

The colloidal particles can be coated. Suitable coating materials include, but are not limited to an antimicrobial material, an antiplatelet material, a fibrinolytic material, a tactifying material, an antibacterial material, a cancer therapeutic, at least one ligand and combinations thereof. Suitable antimicrobial materials include but are not limited to silver containing compounds, lincosamides (for example clindamycin), tetracyclines (for example doxycline or minocycline), fluoroquinolones (for example ciprofloxacin, ofloxacin, levofloxacin or norfloxacin), aminoglycosides (for example streptomycin, tobramycin, gentamycin, or amikacin), and other antimicrobial materials. Suitable antiplatelet or anticoagulation materials include, but are not limited to, dextran, abciximab, clopidogrel, aspirin or other suitable antiplatelet materials. Suitable fibrinolytic materials include, but are not limited to, tissue plasminogen activator, plasmin, urokinase plasminogen activator or other fibrinolytic materials. Suitable tactifying materials include, but are not limited to, hydrophilic and hydrophobic, positively or negative charged or uncharged, moieties to enhance interaction with surface. Suitable antibacterial materials include, but are not limited to, surfactants, rifampin, chlorhexidine, sulfadiazine, erythromycin, or other antibacterial materials. In some embodiments, ligands for receptors expressed on the endothelial cells can be conjugated to the microbots. Suitable ligands include, but are not limited to, selectins, MAC-1. The ligands can be conjugated to the microbot by physical adsorption or covalent coupling. Chemotherapy materials can be used to provide localized chemotherapy to a patient. One skilled in the art would understand that they type of cancer therapeutic material provided to the patient will depend upon multiple factors, including the type of cancer, the biology of the cancer and the biology of the patient. Thus, while an exhaustive list is not included, one skilled in the art would understand that any conjugated medicine can be used. The colloidal particles can also include a material or coating, or be treated, to change the charge associated with the surface. By way of example, the charge of the microbot can be treated to make it anionic, cationic or neutral.

The surface of the colloidal particles, and thereby the microbot, can be smooth. In some embodiments, the surface of the colloidal particles can be decorated with other materials to increase the surface area of the microbot, thereby increasing traction of the microbot. The decoration materials can be adhered to the surface of the colloidal particles. In some embodiments, the decoration materials can have smaller dimensions from the dimension of the colloidal particle that it covers. The surface of the colloidal particles can also be manipulated during the formation of the particles to increase the surface area. For example, the surface of a colloidal particle can be adjusted by changing the synthesis of the particle. The surface of the colloidal particles can also be removed to roughen the surface by chemical etching or by surface roughening (e.g. abrasive blasting, or particle on particle roughening).

A single colloidal particle can form a microbot, but in some embodiments, at least two colloidal particles are joined together to make the microbot. The number of colloidal particles will depend upon the application of the microbots. While there is no maximum limit on the number of colloidal particles used to form a microbot, in some embodiments, between 1 to about 500 colloidal particles are joined to make the microbots. In some embodiments, three colloidal particles are joined to make the microbot. Multiple colloidal particles of the same size or of different sizes can be used to form a microbot. The dimensions of the microbot can dependent upon the number and size of the colloidal particles used. The dimensions of the colloidal particles are limited by the use of the microbots. For example, if the microbot will be used in a vascular system of a patient, the dimensions of the colloidal particles are limited by the dimension of the vein or artery along which the microbot travels. The diameter of the colloidal particles can be between about 1 µm to about 4 µm. In some embodiments, the diameter of the colloidal particles can be between about 10 nm to 10 µm. In some embodiments, the microbot can have a diameter between about 10 nm and about 10 mm. The thickness of the microbot can be between about 10 nm and about 10 µm.

The magnetic fields can have a magnitude between about 1 mT to about 20 mT, however fields outside that range can also be effective. The magnitude can be local to the colloidal particles. One skilled in the art would understand that the magnetic field is dictated by the susceptibility of the colloidal particles. Thus, if a colloidal particle is receptive to a magnetic field, then a lower magnetic field can be used, while if the colloidal particle is not receptive to the magnetic field, then a higher magnetic field should be used. The magnetic field can be used to form, power and direct the microbot. The microbots form quickly after the magnetic field is applied, in some embodiments in less than about 20 seconds. In some embodiments, the microbot forms in between about 0.1 second to about 20 seconds. Furthermore, the colloidal particles can closely pack together (similar to a hexagonal crystalline structure) once the magnetic field is applied. Once the magnetic field is applied to the colloidal particles to form the microbot, the microbot can move (i.e. translating along the surface) at a rolling or translation velocity (V) of between about 1 µm/s and about 1 mm/s. In some embodiments, the microbot can move at a speed greater than about 1 mm/s. The microbot can be moved using a propulsion system. In some embodiments, the propulsion system can be a wall-based propulsion system. The microbot can advance through the patient at a camber angle relative to the wall or tissue, theta. Theta can be between about 0° (i.e. upright orientation compared to the surface) and 90° (i.e. laying flat on the surface). Notably, the microbot can roll along a surface regardless of the camber angle. However, larger camber angles allow the microbots to roll on round surfaces, such as the inner surface of a tube or vessel. The angle for theta can be set using the magnetic field, understanding that the camber angle can change as the microbot travels along a surface that changes (i.e. bumps, turns, etc.). The microbot can apply a force to the surface which it travels on of between about 250 fN to about 25 pN. The coefficient of friction as the microbot is moving within the patient can be between zero and unity.

Important parameters influencing the rolling velocity (V) include the number of particles comprising the microbot (n), its angular frequency ($\omega$), and, as the mirobot rotates, the outer circumferential velocity Vo>$\omega$R.

The microbot can rotate between about 1 hertz and about 100 hertz ($\omega$). Thus, the microbot can be used to remove material with rotational advancement of the microbot.

The magnetic field can be applied using any suitable device. By way of example only, the device can be large, similar to a CT or MRI. In some embodiments, the microbot can be observed in situ using a MRI or other magnetic imaging device. Magnets within these devices can be used to control the microbots. In some embodiments, the magnetic field device can be small, such that it can be used in remote areas or for ease of use. A plurality of electromagnetic coils can be used to apply a magnetic field. The phase angle, $\varphi$, of the field applied to the microbot can be controlled by a user, for example with a device similar to a joystick, or directional keys. Application of the magnetic field can also direct the microbot. Thus, the magnetic field can control the rotational speed, the advancing speed, the angle relative to the wall, theta and the direction of the microbot. Once the magnetic field is removed from the microbots, they can return to the colloidal particle form, and can be absorbed or broken down by white blood cells in the patient.

An aspect of the invention is a method for using a microbot. The method includes inserting at least one particle in a biological system of a patient. A magnetic field is applied to the particles to form the microbot. The microbot is directed to a location in the biological system of the patient.

The microbot can be used to provide material to a location within a patient. Medications can include, but are not limited to, an antimicrobial material, an antiplatelet material, a fibrinolytic material, a tactifying material, an antibacterial material, a cancer therapeutic, at least one ligand and combinations thereof. Suitable antimicrobial materials include but are not limited to silver containing compounds, lincosamides (for example clindamycin), tetracyclines (for example doxycline or minocycline), fluoroquinolones (for example ciprofloxacin, oflozacin, levofloxacin or norfloxacin), aminoglycosides (for example streptomycin, tobramycin, gentamycin, or amikacin), and other antimicrobial materials. Suitable antiplatelet or anticoagulation materials include, but are not limited to, dextran, abciximab, clopidogrel, aspirin or other suitable antiplatelet materials. Suitable fibrinolytic materials include, but are not limited to, tissue plasminogen activator, plasmin, urokinase plasminogen activator or other fibrinolytic materials. Suitable tactifying materials include, but are not limited to, hydrophilic and hydrophobic, positively or negative charged or uncharged, moieties to enhance interaction with surface. Suitable antibacterial materials include, but are not limited to, surfactants, rifampin, chlorhexidine, sulfadiazine, erythromycin, or other antibacterial materials. In some embodiments, ligands for receptors expressed on the endothelial cells can be conjugated to the microbots. Suitable ligands include, but are not limited to, selectins, MAC-1. The ligands can be conjugated to the microbot by physical adsorption or covalent coupling. Chemotherapy materials can be used to provide localized chemotherapy to a patient. One skilled in the art would understand that they type of cancer therapeutic material provided to the patient will depend upon multiple factors, including the type of cancer, the biology of the cancer and the biology of the patient. Thus, while an exhaustive list is not included, one skilled in the art would understand that any conjugated medicine can be used. The microbot can also include a material or coating, or be treated, to change the charge associated with the surface. By way of example, the charge of the microbot can be treated to make it anionic, cationic or neutral.

In some embodiments, the microbot can be used to remove a blockage or occlusion within a patient. The microbot can be used to remove the blockage or can be used to supply medication to the blockage. Advantageously, the materials of the microbots can be broken down by white blood cells within the patient after use.

The magnetic fields can have a magnitude between about 1 mT to about 20 mT, however fields outside that range can also be effective. The magnitude can be local to the colloidal particles. One skilled in the art would understand that the magnetic field is dictated by the susceptibility of the colloidal particles. Thus, if a colloidal particle is receptive to a magnetic field, then a lower magnetic field can be used, while if the colloidal particle is not receptive to the magnetic field, then a higher magnetic field should be used. The magnetic field can be used to form, power and direct the microbot. The microbots form quickly after the magnetic field is applied, in some embodiments in less than about 20 seconds. In some embodiments, the microbot forms in between about 0.1 second to about 20 seconds. Furthermore, the colloidal particles can closely pack together (similar to a hexagonal crystalline structure) once the magnetic field is applied. Once the magnetic field is applied to the colloidal particles to form the microbot, the microbot can move (i.e. translating along the surface) at a rolling or translation velocity (V) of between about 1 μm/s and about 1 mm/s. In some embodiments, the microbot can move at a speed greater than about 1 mm/s. The microbot can be moved using a propulsion system. In some embodiments, the propulsion system can be a wall-based propulsion system. The microbot can advance through the patient at a camber angle relative to the wall or tissue, theta. Theta can be between about 0° (i.e. upright orientation compared to the surface) and 90° (i.e. laying flat on the surface). Notably, the microbot can roll along a surface regardless of the camber angle. However, larger camber angles allow the microbots to roll on round surfaces, such as the inner surface of a tube or vessel. The angle for theta can be set using the magnetic field, understanding that the camber angle can change as the microbot travels along a surface that changes (i.e. bumps, turns, etc.). The microbot can apply a force to the surface which it travels on of between about 250 fN to about 25 pN. The coefficient of friction as the microbot is moving within the patient can be between zero and unity.

The microbot can be used in multiple biological systems in a patient. Systems can include the cardiovascular system, the gastrointestinal system, the lymphatic system, the reproductive system, or other systems within a patient. By way of example, the microbot can be used to remove or reduce a clot (blood, fat, gas, or foreign material) in a patient's artery or vein, or junction between the cardiovascular system and an organ. In some embodiments, the microbot can be used to remove an occlusion in the fallopian tubes of the reproductive organs. In some embodiments, the microbots can be used to remove fluid or metabolic waste from tissues of the lymphatic system. Similar to the vascular system, the microbot would be injected into the lymphatic system. Microbots can also be used to remove a clot in a gastrointestinal system, for example a blockage or occlusion in the small or large intestine. The microbot can also be used within tissue rather than a vessel wall. The patient can be any animal, including a human, dog, cat, horse, cattle, mouse, hamster, or the like.

The microbot can be used to provide medication or treatment to a location in the patient. The medication can be an antimicrobial material, an antiplatelet material, a fibrinolytic material, a tactifying material, an antibacterial material, a cancer therapeutic, at least one ligand or combinations thereof. By way of example, the microbot can provide a cancer therapeutic to a tumor within a patient.

In some embodiments, the microbot can induce localized hyperthermia with a patient. Babincova et al., Selective treatment of neoplastic cells using ferritin-mediated electromagnetic hyperthermia, Medical Hypothesis, 54, 179 (2000), which is incorporated by reference in its entirety, discusses hyperthermic approaches to cancer treatment. The microbots can also be used as paramagnetic particles. Lanza et al., Magnetic resonance molecular imaging with nanoparticles, J. Nucl Cardiol, 11, 733, (2004), which is incorporated by reference, discusses use of iron oxide based materials as contrast enhancers in magnetic imaging.

FIG. 1 illustrates an example application where an external magnetic field is used to assemble microbots, then used for a blood clot removal in a blood vessel. The colloidal particles 102 are joined to make a microbot 104. The colloidal particles rapidly assemble and rotate and employ available surfaces to translate to the clot site 106 in a blood vessel 108. After mechanical or chemical clot dissolution, the applied field is removed and the microbot 108 disassembles into the colloidal particles 102, which quickly disperse.

Figure 2:
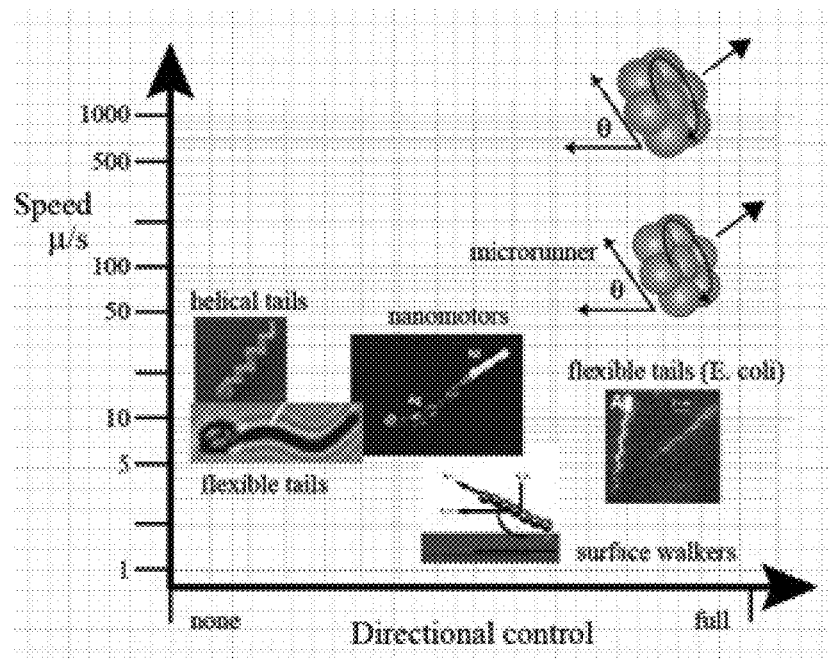
FIG. 2 illustrates the potential speed of several devices compared to the microbot of the present invention.

FIG. 2 illustrates the potential translation velocity of several devices compared to the microbot of the present invention. The microbot of the present invention can have 1-2 orders of magnetite faster speed of the device compared to current technologies. Furthermore, the present invention has much better directional control compared to prior art methods. Thus, as illustrated in FIG. 2, the present invention provides both better directional control and higher speed compared to prior art devices.

EXAMPLES

Figure 3:
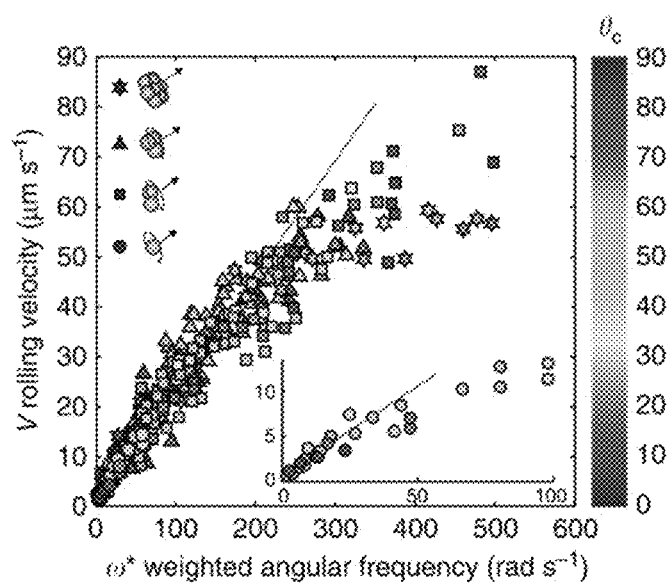
FIG. 3 illustrates the rolling velocity for microbots created from 1 (n=25), 2 (n=168), 3 (n=140) and 7 (n=35) colloidal particles as a function of weighted angular frequency.

FIG. 3 illustrates the rolling velocity for microbots created from 1 (n=25), 2 (n=168), 3 (n=140) and 7 (n=35) colloidal particles as a function of weighted angular frequency. Weighted angular frequency is represented in Equation 1.

$$\omega^* \omega \cdot n \cdot \cos(\theta_c) \tag{1}$$

Figure 4:
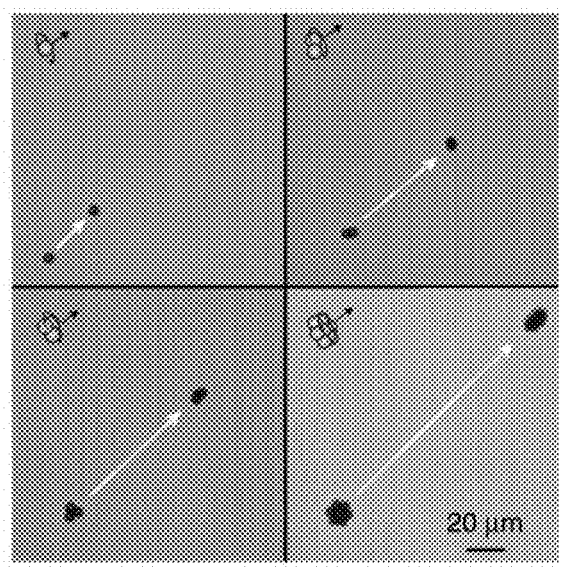
FIG. 4 illustrates three seconds of translation under identical field conditions demonstrate that larger microbots roll faster.

Data points oriented upright (0°) to lying nearly flat (90°). Line indicates the slope (3 mg/32η) (where η is viscosity) based on wet friction scaling arguments. To compare results for spherical monomers with those for disk-like wheels, the drag force ($F_d$) was used for spheres at low Reynolds number (Re) (Equation 2). V, which is related to the friction coefficient, was determined from Equation 3.

$$F_d = 6\pi\eta RV \tag{2}$$

$$V = (mg/6\pi\eta)(\eta/hP)\cdot\omega\cdot n\cdot\cos(\theta_c) \tag{3}$$

where R is the radius of the microbot, h is the gap between the microbot and the surface with pressure P (load/area). The monomer results are scaled by $32/(3\cdot6\pi)=16/9\pi$ inset shows unscaled monomer data. FIG. 4 illustrates three seconds of translation under identical field conditions demonstrate that larger microbots roll faster. The increased angular frequency and lower camber angles lead to increased speeds as well. The weighted angular frequency illustrated in FIG. 3 accounts for microbot size and angular frequency. The data illustrates good agreement with this scaling for weighted angular frequencies below 200 rad s/l. Above this amount, the scaling deviates from the data, likely because the assumption that the microbot velocity is much greater than the fluid velocity is no longer valid. Microbots roll along the surface at speeds of up to 90 μm/s with applied field frequencies up to 50 Hz over the 0°<$\theta_c$<90°. Even single particles roll as long as the surface-parallel component of the rotational axis is not zero. Microbots comprising 2, 3, 7 and even 19 particles, though not strictly round, exhibit smooth motion as they rapidly spin and translate across flat surfaces as illustrated in FIG. 4. At higher values, motion becomes unstable. Velocities of greater than 120 μm/s were achieved with dimers and 19-mers at higher amplitude fields, but observation times were limited due to the size of the field-of-view. The data condense to a single line at low to moderate ω as illustrated in FIG. 3, which supports the conclusion that friction is not stick-slip and microbot speeds increase with size for a given angular frequency due both to the increased load and increased fluid velocities near the wall. A useful feature of this approach is that different sized microbots, and thus different speeds for a given field rotation frequency, can be assembled from the same building blocks by changing the bulk colloid concentration. In fact, microbots of other particle sizes roll well. However, structural isomers in these systems make quantification difficult.

Figure 5A:
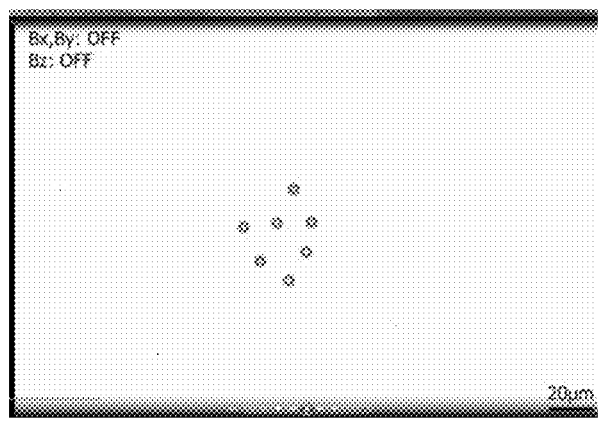
FIG. 5A illustrates the formation of a microbot initially.
Figure 5B:
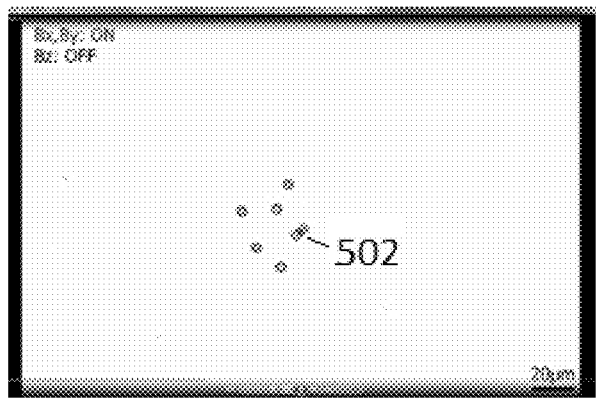
FIG. 5B illustrates the particles after the $B_x$ and $B_y$ magnetic fields are turned on and time elapses.
Figure 5C:
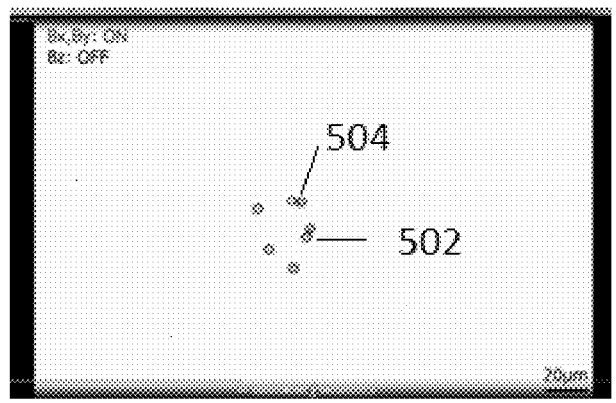
FIG. 5C illustrates two additional particles joining together continued from FIG. 5B.
Figure 5D:
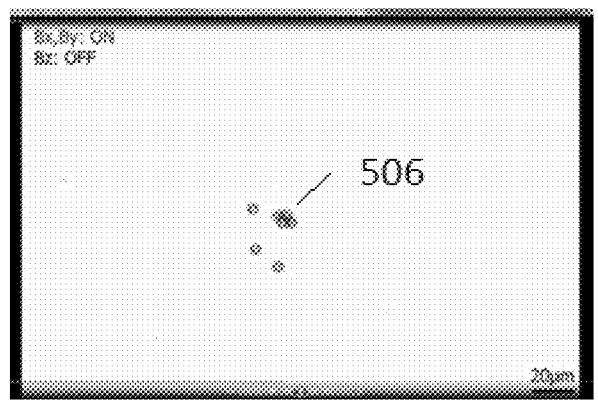
FIG. 5D illustrates the formation of a four particle microbot continued from FIG. 5C.
Figure 5E:
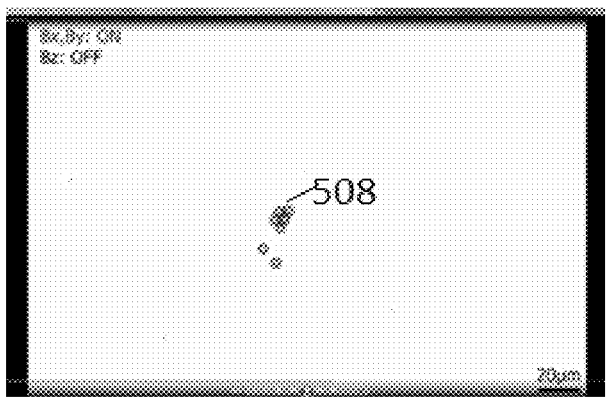
FIG. 5E illustrates the formation of a five particle microbot continued from FIG. 5D.
Figure 5F:
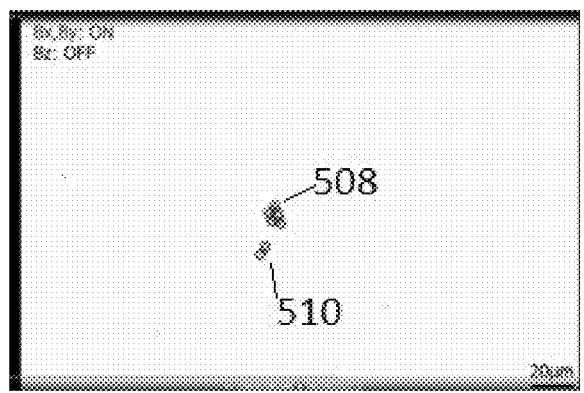
FIG. 5F illustrates the two remaining microbots joining together to form a two particle microbot near the five particle microbot of FIG. 5E.
Figure 5G:
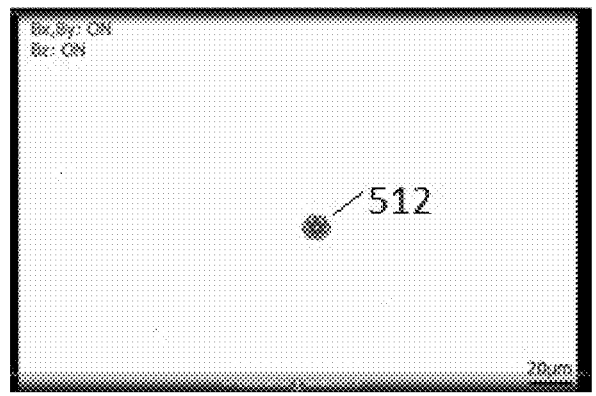
FIG. 5G illustrates a seven particle microbot continued from FIG. 5F.

FIGS. 5A-G illustrate the forming of a microbot. Seven colloidal particles are illustrated in these figures. Three magnetic fields $B_x$, $B_y$, and $B_z$ are initially off as illustrated in FIG. 5A. FIG. 5B illustrates the particles after the $B_x$ and $B_y$ magnetic fields are turned on and time elapses. Two particles have joined in FIG. 5B (illustrated as 502). While not illustrated in these figures, the particles are rotating at a rotational velocity ($\omega$). FIG. 5C illustrates two additional particles joining together (illustrated as 504) after additional time elapses. FIG. 5D illustrates the joining of 502 and 504 to form a four particle microbot (illustrated as 506) after additional time elapses. FIG. 5E illustrates an additional particle joining the microbot 506 to form a five particle microbot (illustrated as 508) after additional time elapses. FIG. 5F illustrates the two remaining microbots joining together to form a two particle microbot 510 after additional time elapses. Finally, FIG. 5G illustrates a seven particle microbot 512 formed from the joining of 510 and 508 after additional time elapses. The $B_z$ magnetic field has also been activated. A total of about 12 second elapsed from the time that the magnetic field was applied (illustrated in FIG. 5B) to the forming of the seven-mer microbot (illustrated in FIG. 5G).

Figure 6A:
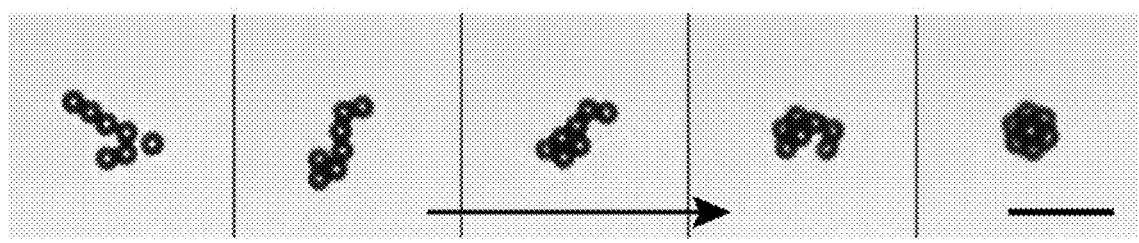
FIG. 6A illustrates seven colloidal particles as they form a microbot.
Figure 6B:
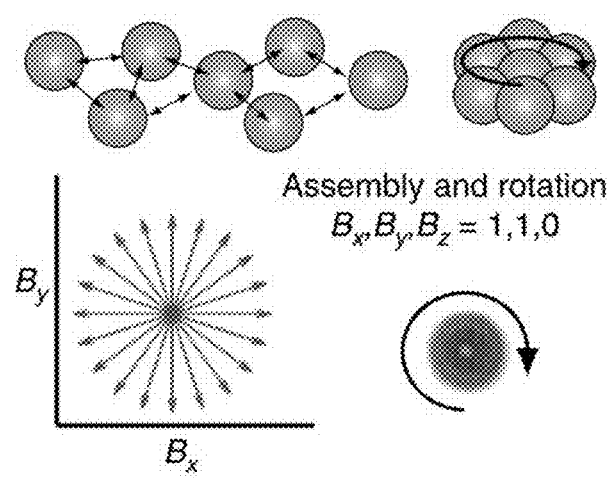
FIG. 6B illustrates the assembly and rotation of the microbot.
Figure 6C:
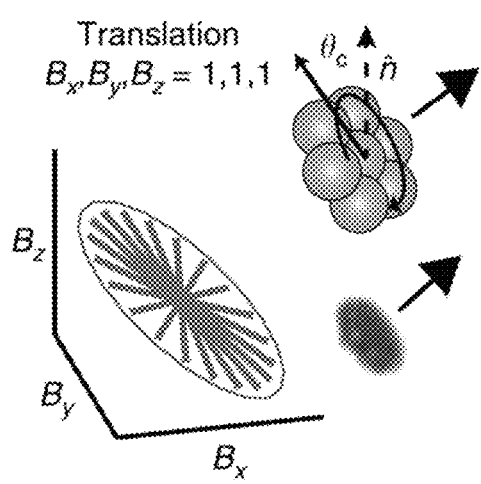
FIG. 6C illustrates the translation of the microbot.
Figure 6D:
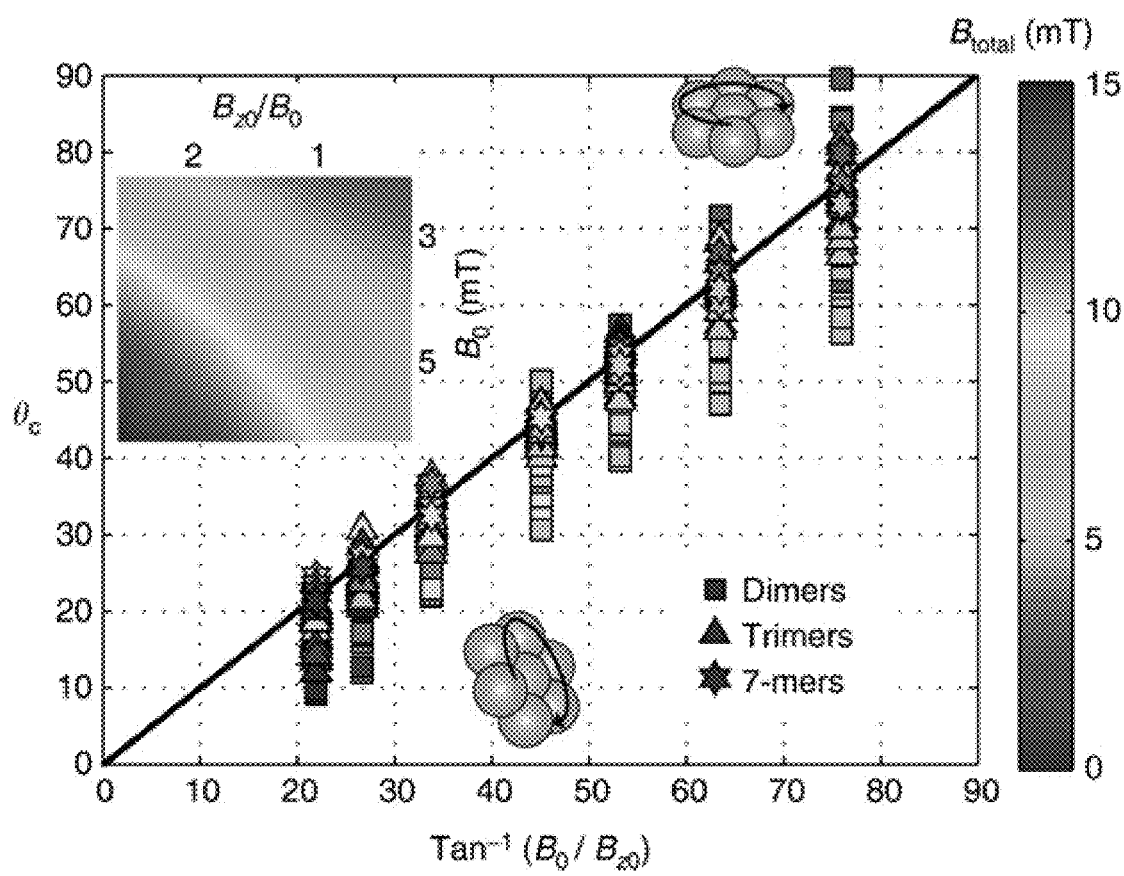
FIG. 6D illustrates the camber angle function of the magnetic field in the direction perpendicular to the wall.

FIGS. 6A-D illustrates field induced assembly and rotation of a seven-mer microbot. Superparamagnetic beads assemble into a microbot by isotropic interactions induced by the in-plane rotating magnetic field (FIG. 6A-B) with microbot size controlled by local bead density. Spinning microbots lying flat on a surface have no net motion. For translation to occur they must be inclined relative to the surface. A normal component is introduced to the magnetic field to orient the field rotation axis towards the surface plane and propel the microbot. With addition of a field in the z direction, both symmetric and asymmetric microbots reorient off the surface to a defined camber angle, $\theta_c$ (FIG. 6C-D), and begin to translate. Advantageously, the camber angle can vary from lying flat, (90°), and spinning without translation to fully upright, (0°), and rolling (FIG. 6B-C). FIG. 6A illustrates the formation of the microbot. Seven colloidal particles join together to form the microbot. With application of the rotating magnetic field $B_x+B_y$ in the surface plane, colloids assemble via isotropic interactions and 'sit and spin' (scale bar, 20 µm) as illustrated in FIG. 6B. FIG. 6C illustrates the field rotation axis oriented towards the surface plane resulting in the microbots 'standing up' at a camber angle, $\theta_c$, and roll along the surface with addition of a normal variable-phase component ($B_z$). FIG. 6D illustrates $\theta_c$ measured during microbot translation as a function of the applied field rotation axis set via $\tan^{-1}(B_0/B_{z0})$. Data points (n=368) are illustrated by the magnetic field magnitude, from low to high. The magnetic field magnitude is represented by Equation 4.

$$B_{Total}=(B_0^2+B_{z0}^2)^{1/2} \quad (4)$$

The black line corresponds to perfect alignment between microbot and field rotation axis. The inset identifies total field magnitudes as field ratios are varied.

Figure 7:
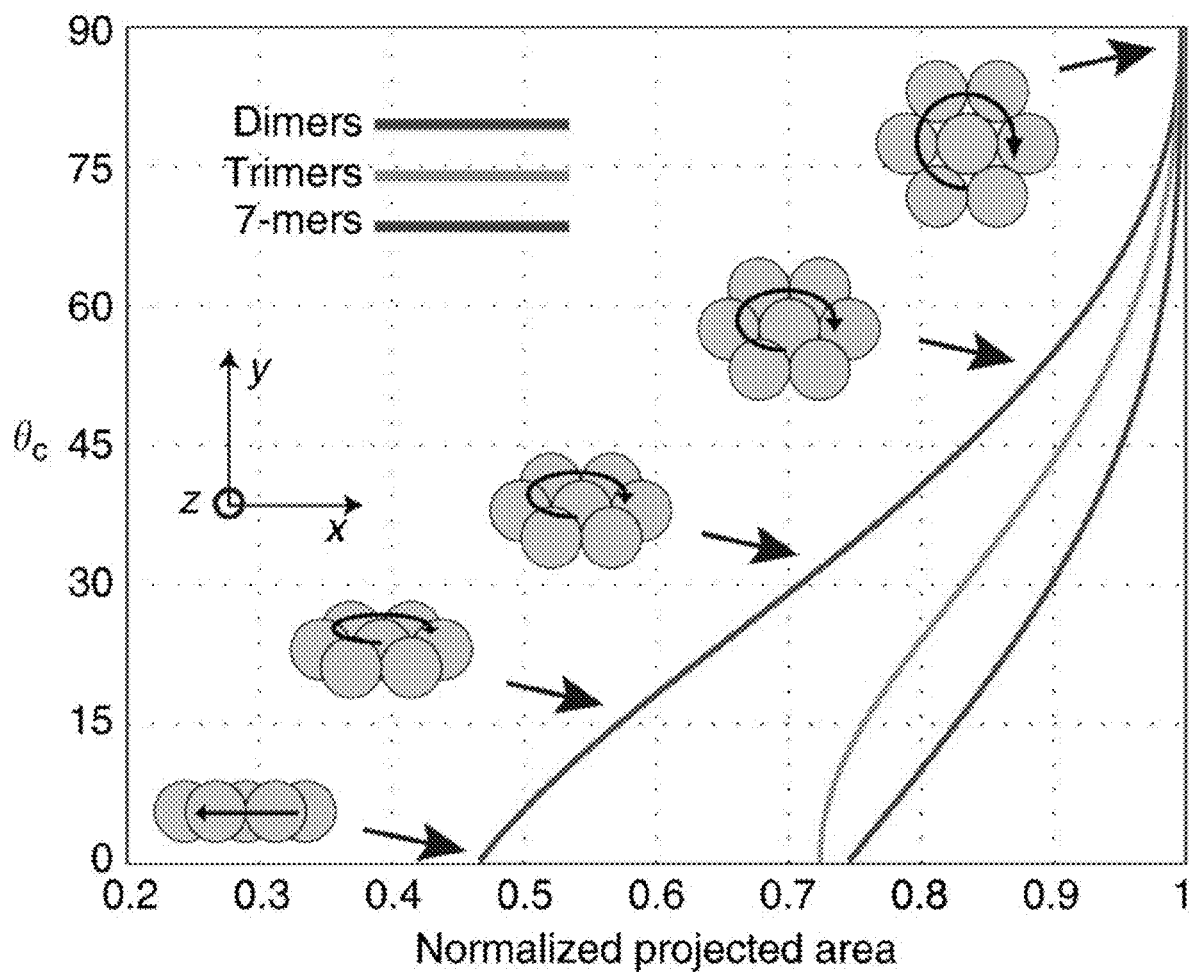
FIG. 7 illustrates the camber angle curves as a function of microbot projected area as viewed from above for several configurations of microbots.

FIG. 7 illustrates the camber angle curves as a function of microbot projected area as viewed from above for several configurations of microbots.

Figure 8A:
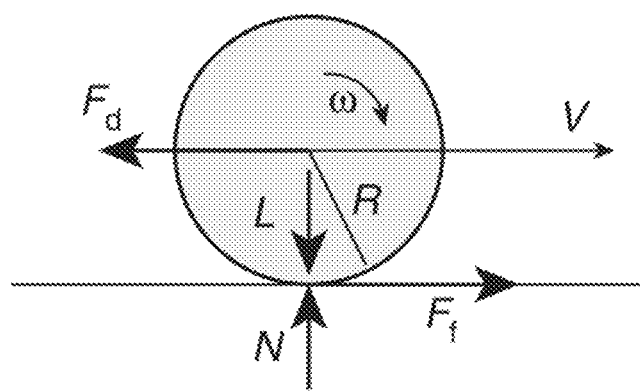
FIG. 8A illustrates a side view and of a translating microbot modeled as a disk.
Figure 8B:
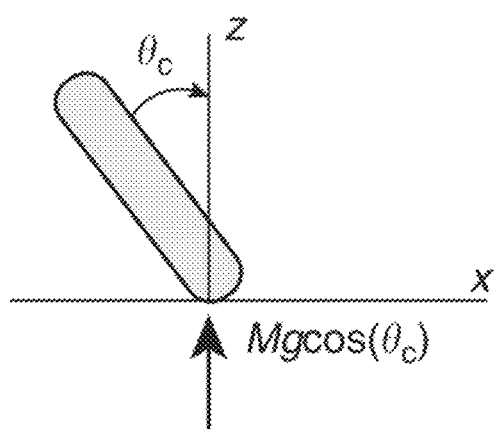
FIG. 8B illustrates a front view of a translating microbot modeled as a disk.

FIGS. 8A and 8B illustrate a side view and front view, respectively, of a translating microbot modeled as a disk. The important parameters include $F_d$, drag force; $F_f$, friction force; L, load; N, normal force from wall; M, mass of the microbot; $\theta_c$, camber angle; $\omega$, angular frequency; g, gravitational constant; and R, radius.

Figure 9A:
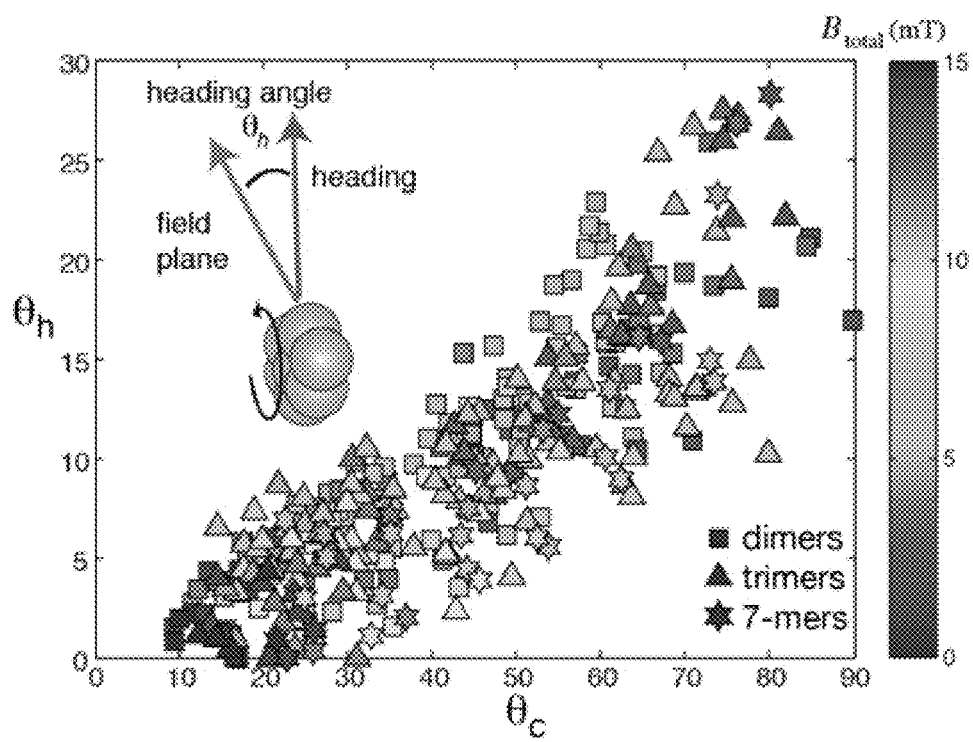
FIG. 9A illustrates heading angle as a function of camber angle.
Figure 9B:
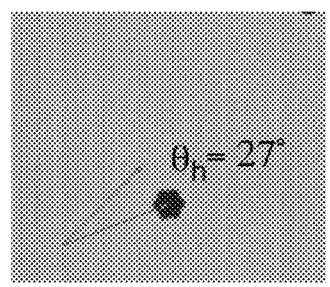
FIG. 9B illustrates the heading angle of 27°.
Figure 9C:
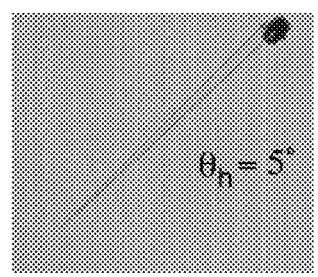
FIG. 9C illustrates a heading angle of 5°.

FIGS. 9A-C illustrates the heading angle. Targeting applications require not only microbot propulsion but also the ability to direct them to desired locations. Unlike tires, microbots can be oriented at very high $\theta_c$ and, as a result, can experience significant lateral forces and heading slip. Defining the heading slip angle, $\theta_h$, as the difference between the rolling direction (heading) and the microbot rotation plane (pointing) directions, lateral forces can be observed to push microbots towards the microbot rotational axis (FIG. 9A). As $\theta_c$ increases, heading and pointing directions separate as characterized by increasing microbot heading angle $\theta_h$ (n=343) as illustrated in FIG. 9A. FIG. 9B illustrates a microbot where $\theta_h$ is 27°, $\theta_c$ is 76°, and V is 14 µm/s. FIG. 9C illustrates a microbot where the heading angle is 5°, $\theta_c$ is 28° and V is 39 µm/s.

Figure 10A:
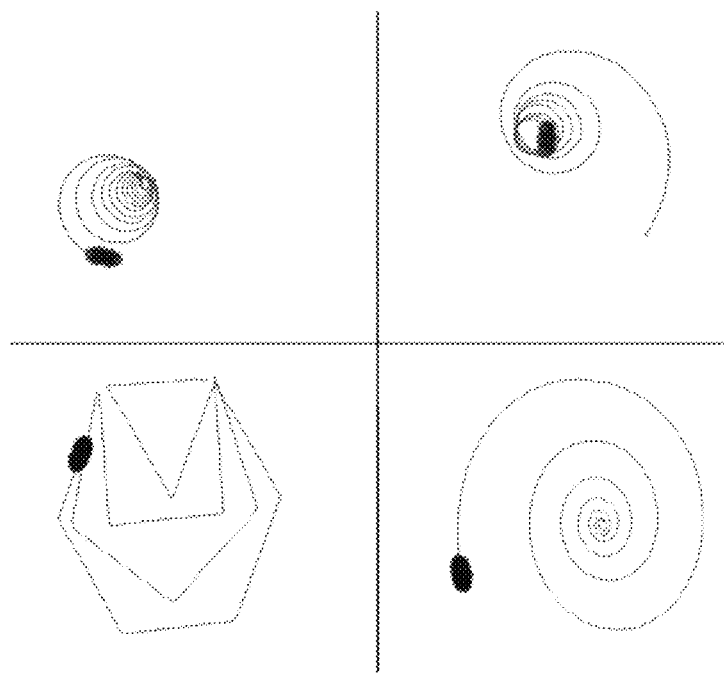
FIG. 10A illustrates automated patterns of a microbot.
Figure 10B:
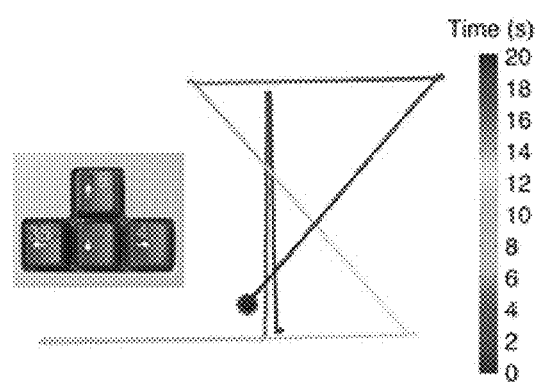
FIG. 10B illustrates a manual pattern of a microbot.
Figure 10C:
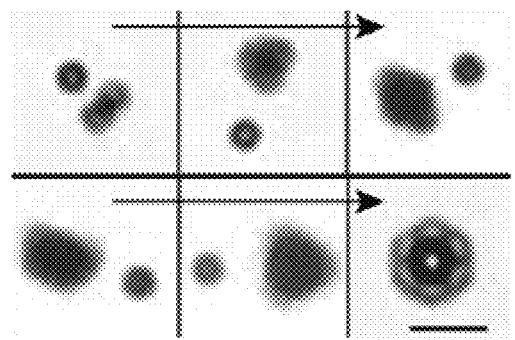
FIG. 10C illustrates a stepwise microbot assembly.

FIGS. 10A-C illustrate directional control of the microbots. FIG. 10A illustrates automated patterns that can be formed with the microbots of the invention (scale bars, 10 µm). FIG. 10B illustrates manual control of the microbots using a keypad over time. FIG. 10C illustrate a stepwise microbot assembly.

Figure 11A:
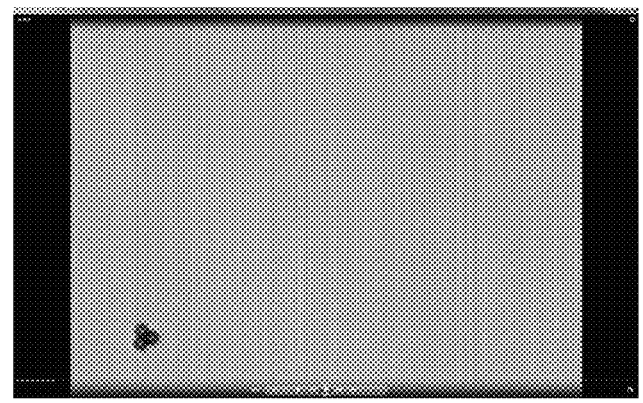
FIG. 11A illustrates a microbot comprising three colloidal particles at a first position.
Figure 11B:
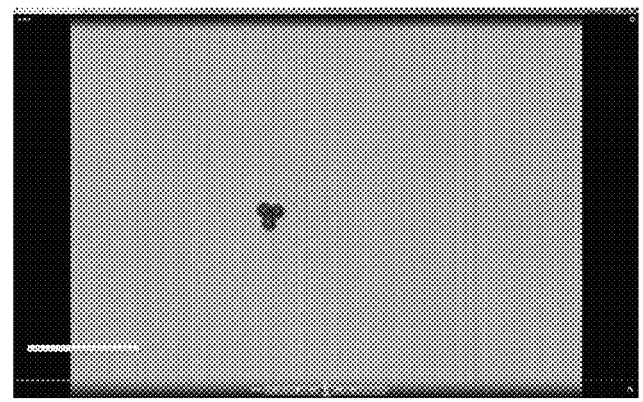
FIG. 11B illustrates a microbot comprising three colloidal particles at a second position.
Figure 11C:
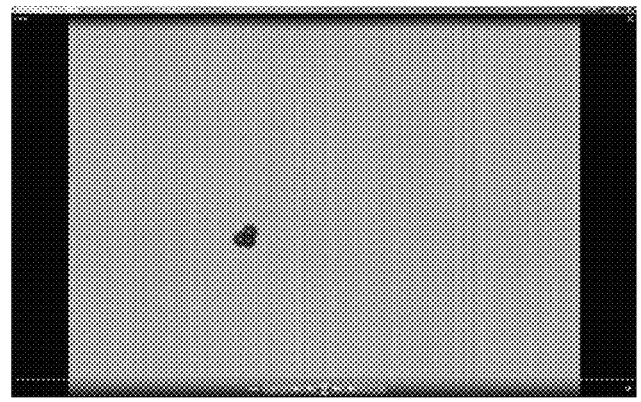
FIG. 11C illustrates a microbot comprising three colloidal particles at a third position.
Figure 12A:
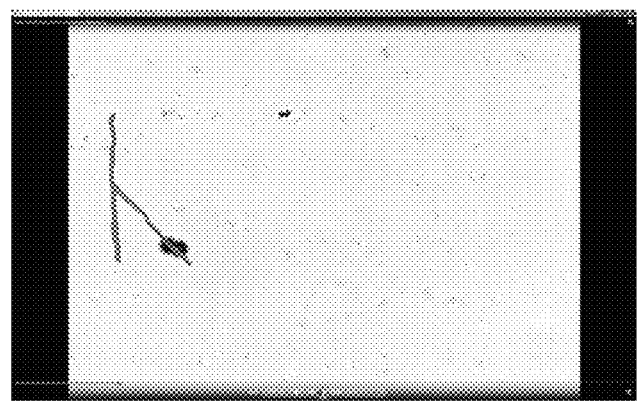
FIG. 12A illustrates a microbot comprising two colloidal particles at a first position.
Figure 12B:
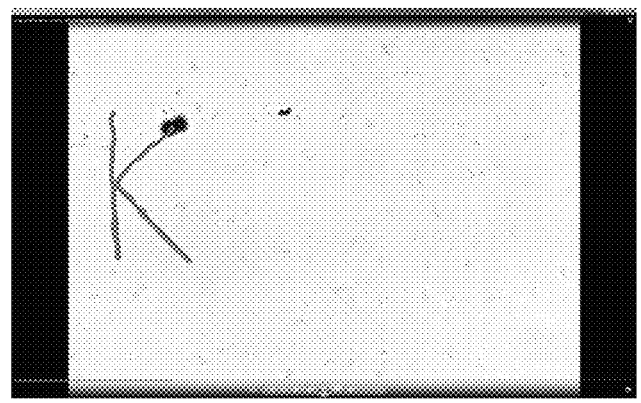
FIG. 12B illustrates a microbot comprising two colloidal particles at a second position.
Figure 12C:
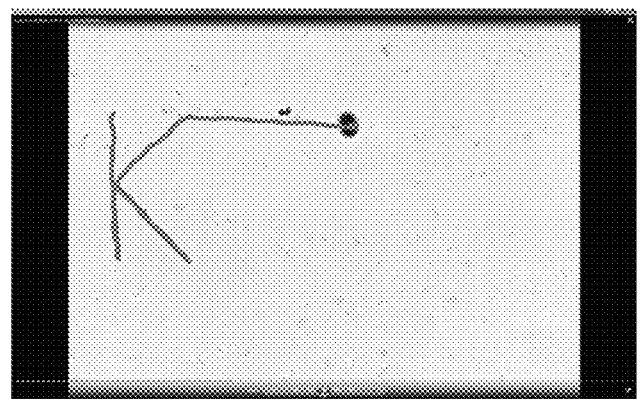
FIG. 12C illustrates a microbot comprising two colloidal particles at a third position.
Figure 12D:
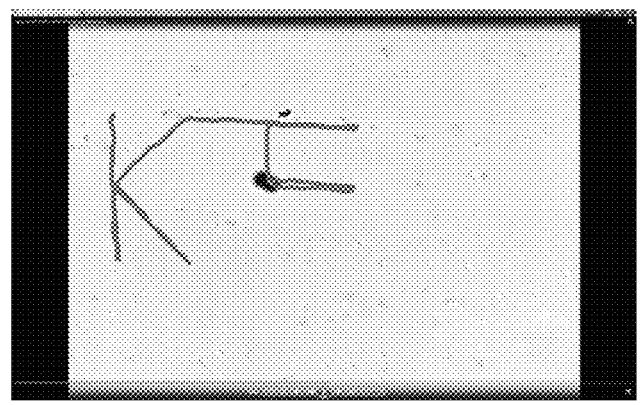
FIG. 12D illustrates a microbot comprising two colloidal particles at a fourth position.
Figure 12E:
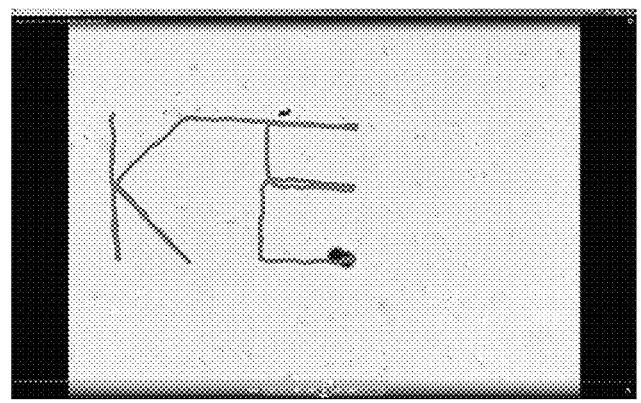
FIG. 12E illustrates a microbot comprising two colloidal particles at a fifth position.
Figure 12F:
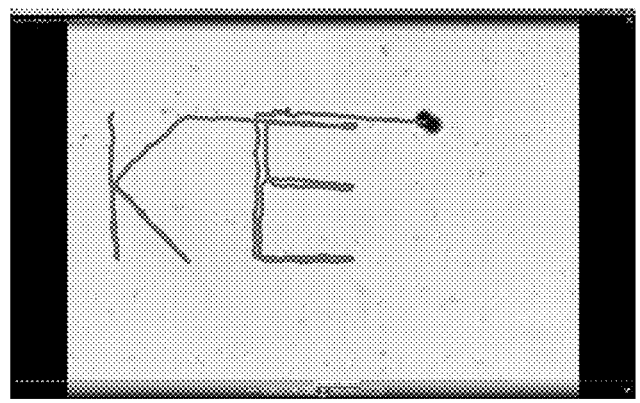
FIG. 12F illustrates a microbot comprising two colloidal particles at a sixth position.
Figure 12G:
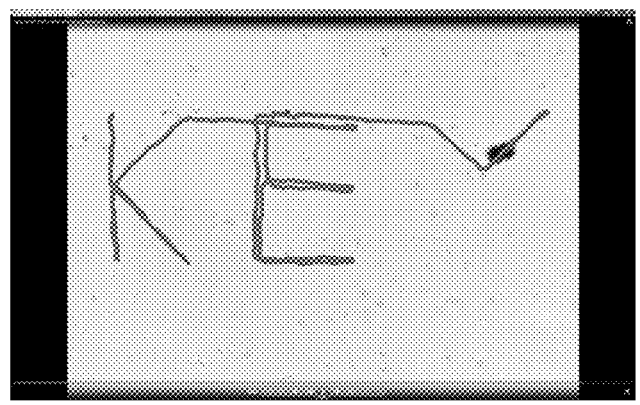
FIG. 12G illustrates a microbot comprising two colloidal particles at a seventh position.
Figure 12H:
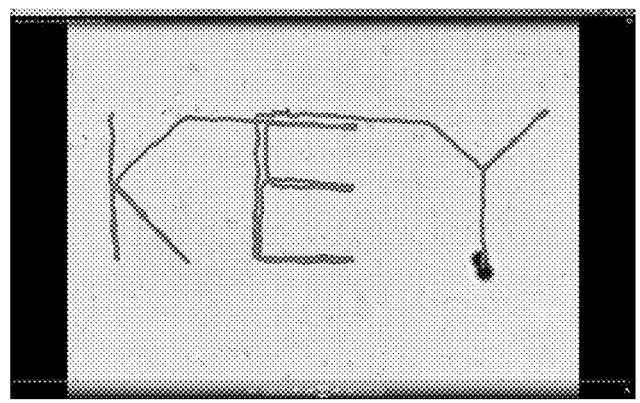
FIG. 12H illustrates a microbot comprising two colloidal particles at an eighth position.

FIGS. 11A, 11B and 11C illustrate a microbot comprising three colloidal particles that have been moved from a first position (FIG. 11A) to a second position (FIG. 11B) to a third position (FIG. 11C).

FIGS. 12A-H illustrate a microbot comprising two colloidal particles that have been moved from a first position (FIG. 12A) to a final position (FIG. 12H) and intermediate positions (FIGS. 12B-G). For clarity, the path of the microbot has been illustrated by spelling the word "key."

Figure 13:
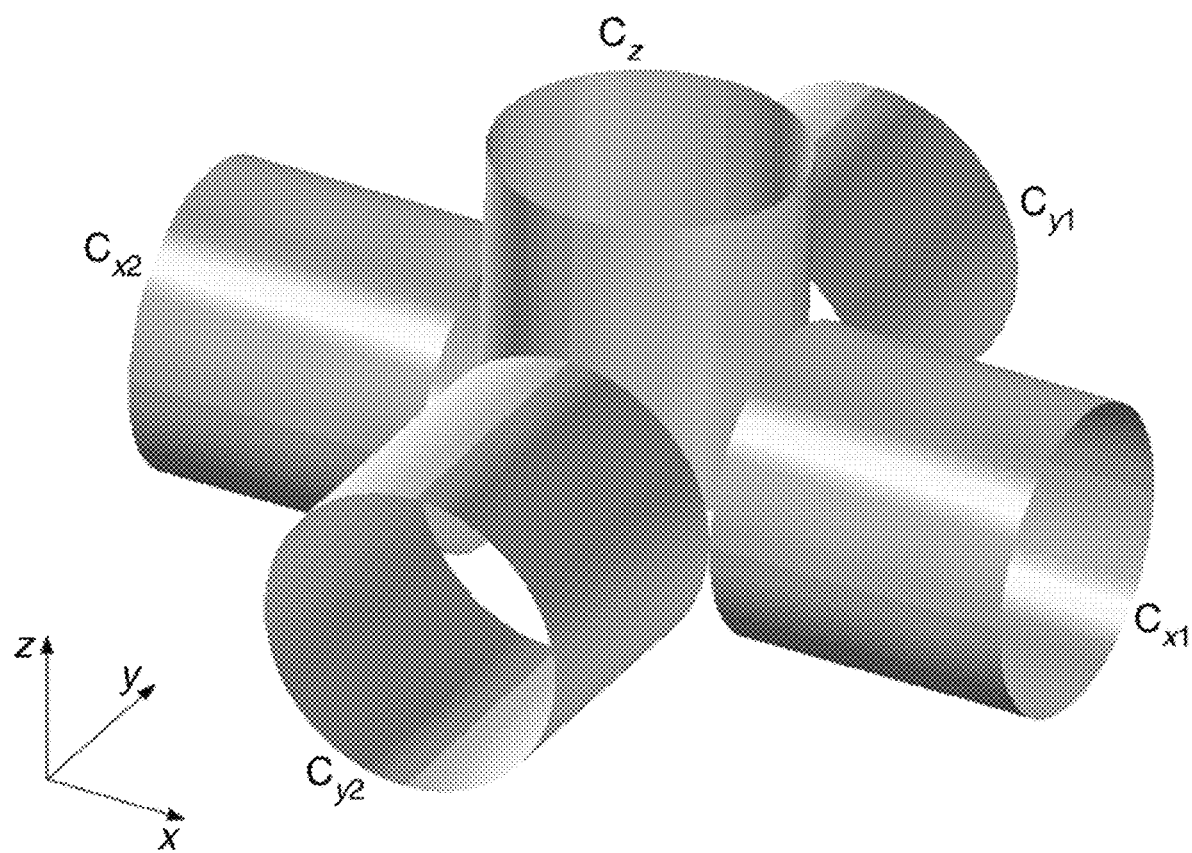
FIG. 13 illustrates an experimental set up of the invention where the magnetic field system consists of five air-cored solenoid coils.

FIG. 13 illustrates an experimental set up of the magnetic field system consisting of five air-cored solenoid coils. These cores are used to apply the magnetic field to the microbots. Each coil had an inner diameter of 50 mm, 51 mm length, 400 turns and current capacity 3.5 A. The field generated at the center of experiments had three components, $B_x$, $B_y$ and $B_z$ (equations represented in Equations 5-7, respectively):

$$B_x=/B_{x0}\cos(\omega_f t) \quad (5)$$

$$B_y=B_{y0}\cos(\omega_f t-\pi/2) \quad (6)$$

$$B_z=B_{z0}\cos(\omega_f t-\varphi_z) \quad (7)$$

$B_x$ was generated by coils $C_{x1}$ and $C_{x2}$, $B_y$ was generated by $C_{y1}$ and $C_{y2}$, $B_z$ was generated by coil C. Sinusoidal voltage waveforms were generated using Matlab (Mathworks, Inc., Natick, Mass., USA) and an analog-output card (National Instruments, NI-9263) and then amplified (Behringer EP2000) before being applied to individual solenoids. To monitor coil currents, an analog input data acquisition card was used (National Instruments, NI-USB-6009). The resulting magnetic fields were estimated using a custom Matlab code solving the fields of the solenoids for a given current. Predictions of the code were validated by exciting the coils with constant currents and measuring the field with a gaussmeter (VGM Gaussmeter, Alphalab Inc.).

The effect of rotational speed ($\omega$) on translation velocity tested. Table 1 illustrates the velocity for two-mer microbots.

TABLE 1

| Sample | Number of colloidal particles (n) | Rotational Speed (ω - rotations/s) | Translation velocity (μm/s) | Theta (°) |
|---|---|---|---|---|
| 1 | 2 | 45 | 17 | 17 |
| 2 | 2 | 64 | 28 | 17 |
| 3 | 2 | 126 | 52 | 17 |
| 4 | 2 | 253 | 87 | 17 |
| 5 | 2 | 126 | 22 | 53 |
| 6 | 2 | 126 | 33 | 44 |
| 7 | 2 | 126 | 47 | 24 |
| 8 | 7 | 16 | 14 | 76 |
| 9 | 7 | 19 | 21 | 65 |
| 10 | 7 | 21 | 25 | 53 |
| 11 | 7 | 24 | 28 | 44 |
| 12 | 7 | 28 | 34 | 35 |
| 13 | 7 | 33 | 39 | 28 |

Ranges have been discussed and used within the forgoing description. One skilled in the art would understand that any sub-range within the stated range would be suitable, as would any number within the broad range, without deviating from the invention.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

The invention claimed is:

1. A microbot system for use in a biological system, comprising:
    at least two colloidal particles comprising magnetic properties; and
    a magnetic field activating the at least two colloidal particles to form the microbot system, and propelling the microbot system by rolling the microbot system on a surface that is external to the rotating microbot system with the magnetic field, wherein at least two of the at least two colloidal particles are in contact with each other and remain in contact with each other during the propelling.

2. The microbot system of claim 1, wherein the at least two colloidal particles comprise a paramagnetic material, a superparamagnetic material, a non-magnetic material comprising a magnetic material or combinations thereof.

3. The microbot system of claim 1, wherein the microbot applies a force of between about 250 fN to about 25 pN to a surface.

4. The microbot system of claim 1, further comprising a surface coating.

5. The microbot system of claim 4, wherein the surface coating is at least one of an antimicrobial material, an antiplatelet material, a fibrinolytic material, a tactifying material, an antibacterial material, a cancer therapeutic medicine, or at least one ligand.

6. The microbot system of claim 1, wherein between 2 and 500 of the at least two colloidal particles are joined in the magnetic field to form the microbot.

7. The microbot system of claim 1, further comprising at least one ligand for receptors expressed on an endothelial cell.

8. The microbot system of claim 1, further comprising an anionic surface.

9. The microbot system of claim 1, wherein the at least two colloidal particles vary in size, and wherein a diameter of the at least two colloidal particles vary between about 1 micron and 10 mm.

10. The microbot system of claim 1, wherein the rolling converts rotational energy to translational energy using wall friction.

11. A method to form a rotating microbot, comprising:
    applying a magnetic field to at least two colloidal particles of a diameter between about 1 μm and about 4 μm;
    forming the rotating microbot comprising the at least two colloidal particles in a biological system of a patient in the presence of the magnetic field;
    rotating the rotating microbot by rolling propulsion on a surface that is external to the rotating microbot in the presence of the magnetic field; and
    disassembling the rotating microbot to the at least two colloidal particles when the magnetic field is removed, wherein at least two of the at least two colloidal particles are in contact with each other and remain in contact with each other during the rolling propulsion.

12. The method of claim 11, wherein the magnetic field is between about 1 mT and about 20 mT.

13. The method of claim 11, wherein the microbot forms in between about 1 second and about 20 seconds, and wherein a speed of the rotating microbot is between about 10 μm/s and about 100 μm/s.

14. The method of claim 11, wherein the at least two colloidal particles do not form the microbot in the absence of the magnetic field.

15. A method for using a microbot in a biological system to treat a patient, comprising:
    inserting at least one particle in the biological system of the patient;
    applying a magnetic field to the at least one particle to form the microbot; and
    rolling the microbot to a predetermined location in the biological system of the patient by propelling the microbot as a result of a rotational force created by the magnetic field on a surface that is external to the microbot in the biological system, wherein at least two of the at least one particle are in contact with each other and remain in contact with each other during the propelling.

16. The method of claim 15, further comprising disassembling the microbot by removing the magnetic field.

17. The method of claim 15, wherein the biological system is a cardiovascular system, a lymphatic system, a reproductive system, or a gastrointestinal system.

18. The method of claim 15, wherein the microbot provides a cancer therapeutic medicine to the patient.

19. The method of claim 15, wherein the microbot is directed to the predetermined location in the biological system of the patient with the magnetic field.

20. The method of claim 15, wherein the microbot induces localized hyperthermia.

21. The method of claim 15, wherein the microbot is used to remove at least one occlusion in the patient.

* * * * *